(12) United States Patent
Goll et al.

(10) Patent No.: US 11,723,877 B2
(45) Date of Patent: *Aug. 15, 2023

(54) MICROENCAPSULATION PROCESS AND PRODUCT

(71) Applicant: SPI PHARMA, INC., Wilmington, DE (US)

(72) Inventors: Diane Goll, Grand Haven, MI (US); Cecil W. Propst, Norton Shores, MI (US)

(73) Assignee: SPI PHARMA, INC., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/784,894

(22) Filed: Feb. 7, 2020

(65) Prior Publication Data

US 2020/0170959 A1 Jun. 4, 2020

Related U.S. Application Data

(63) Continuation of application No. 13/825,026, filed as application No. PCT/US2011/052406 on Sep. 20, 2011, now Pat. No. 10,561,621.

(60) Provisional application No. 61/384,351, filed on Sep. 20, 2010.

(51) Int. Cl.

| | |
|---|---|
| *A61K 9/50* | (2006.01) |
| *A61K 9/00* | (2006.01) |
| *A61K 31/167* | (2006.01) |
| *A61K 31/522* | (2006.01) |
| *A61K 31/4402* | (2006.01) |
| *A61K 31/451* | (2006.01) |
| *A61K 31/192* | (2006.01) |
| *A61K 9/20* | (2006.01) |

(52) U.S. Cl.
CPC .......... *A61K 9/5057* (2013.01); *A61K 9/0056* (2013.01); *A61K 9/2081* (2013.01); *A61K 9/501* (2013.01); *A61K 9/5031* (2013.01); *A61K 9/5036* (2013.01); *A61K 9/5042* (2013.01); *A61K 9/5052* (2013.01); *A61K 31/167* (2013.01); *A61K 31/192* (2013.01); *A61K 31/4402* (2013.01); *A61K 31/451* (2013.01); *A61K 31/522* (2013.01)

(58) Field of Classification Search
CPC .. A61K 9/5057; A61K 9/0056; A61K 31/167; A61K 9/501; A61K 31/522; A61K 31/4402; A61K 31/451; A61K 31/192; A61K 9/2081; A61K 9/5031; A61K 9/5036; A61K 9/5042; A61K 9/5052; A61P 1/04

See application file for complete search history.

(56) References Cited

U.S. PATENT DOCUMENTS

| | | | | |
|---|---|---|---|---|
| 4,515,769 | A ‡ | 5/1985 | Merritt et al. | A23G 4/043 131/27 |
| 4,800,087 | A * | 1/1989 | Mehta | A61K 9/0056 424/480 |
| 5,023,024 | A ‡ | 6/1991 | Kyogoku | B01J 13/10 264/4 |
| 5,607,697 | A * | 3/1997 | Alkire | A61K 9/5047 424/495 |
| 5,609,909 | A * | 3/1997 | Meyer | A61K 9/5052 427/2.14 |
| 5,653,993 | A * | 8/1997 | Ghanta | A61K 31/192 424/440 |
| 6,080,412 | A * | 6/2000 | Jordan | A61K 9/5026 424/400 |
| 6,165,512 | A | 12/2000 | Mezaache et al. | |
| 6,951,655 | B2 ‡ | 10/2005 | Cho | A61K 9/5015 424/45 |
| 7,118,765 | B2 ‡ | 10/2006 | Norman et al. | A61K 31/439 424/48 |
| 8,088,403 | B2 ‡ | 1/2012 | Dardelle | B01J 13/08 424/42 |
| 2003/0007997 | A1* | 1/2003 | Lawlor | A23G 3/343 424/440 |
| 2003/0193102 | A1 ‡ | 10/2003 | Yan | A61K 9/501 264/4 |

(Continued)

FOREIGN PATENT DOCUMENTS

| | | | | |
|---|---|---|---|---|
| CA | 2634481 A1 ‡ | 7/2007 | ........... | A61K 9/5015 |
| CA | 2634481 A1 | 7/2007 | | |

(Continued)

OTHER PUBLICATIONS

B. Gaihre et al., "Gelatin-coated magnetic iron oxide nanoparticles as carrier system: Drug loading an in vitro drug release study," International Journal of Pharmaceutics 365 (2009) pp. 180-189.*
Drug Information System, "Dextromethorphan," <http://druginfosys.com/Drug.aspx?drugCode=226&drugName=>, (Copyright 2002-2014), pp. 1-3.*
Examination Report for Japanese Patent Application No. 2013-529420 dated Jul. 31, 2015.‡
"Know-how in preparation of nano / micro-capsules," 2008, p. 48 (Japanese).‡
Examination Report for Chinese Patent Application No. 201180055551.2 dated Feb. 11, 2015.‡
Examination Report for Australian Patent Application No. 2011305572 dated Jan. 15, 2015.‡

(Continued)

*Primary Examiner* — Monica A Shin
(74) *Attorney, Agent, or Firm* — Morgan, Lewis & Bockius LLP

(57) ABSTRACT

A composition comprising a core material, having a taste value and a polymeric coating. The polymeric coating substantially surrounds the core material and comprises a cationic polymer and optionally an anionic polymer. The polymeric coating has a uniform thickness ranging from 2 μm to 20 μm. The composition provides release of a portion of the core material which is taste masked over a time period ranging from 0.5 minute to 2 minutes in the oral cavity and provides a modified-release of the remaining core material in a gastrointestinal tract.

13 Claims, 8 Drawing Sheets

(56) References Cited

U.S. PATENT DOCUMENTS

| | | | |
|---|---|---|---|
| 2006/0251702 A1 | 11/2006 | Janis et al. | |
| 2006/0251716 A1 ‡ | 11/2006 | Norman et al. | ..... A61K 31/167 424/46 |
| 2006/0263423 A1 ‡ | 11/2006 | Norman et al. | ........ A23L 27/34 424/46 |
| 2007/0092562 A1 ‡ | 4/2007 | Norman et al. | ..... A61K 9/2018 424/46 |
| 2008/0107729 A1 ‡ | 5/2008 | Amin et al. | ......... A61K 9/2018 424/46 |
| 2008/0132535 A1 ‡ | 6/2008 | Singh et al. | ............. A61P 25/20 514/30 |
| 2010/0226964 A1 ‡ | 9/2010 | Tillotson et al. | ........ A61P 29/00 424/44 |
| 2011/0038897 A1 ‡ | 2/2011 | Shah | ....................... A61K 31/27 424/40 |
| 2011/0092605 A1 * | 4/2011 | Yan | ......................... B01J 13/10 514/774 |

FOREIGN PATENT DOCUMENTS

| | | | | |
|---|---|---|---|---|
| CN | 1376058 A | ‡ | 10/2002 | ............. A61P 25/00 |
| CN | 1376058 A | | 10/2002 | |
| CN | 1582143 A | | 2/2005 | |
| CN | 1582143 A | ‡ | 2/2005 | ................ A61P 5/00 |
| EP | 0465238 A1 | ‡ | 1/1992 | ............ A61K 9/5089 |
| EP | 0465238 A1 | | 1/1992 | |
| JP | 2005-187416 A | | 7/2005 | |
| JP | 2005-187416 A | ‡ | 7/2005 | |
| KR | 10-2004-0105865 | ‡ | 12/2004 | |
| KR | 10-2004-0105865 A | | 12/2004 | |
| WO | 2003086104 A1 | | 10/2003 | |
| WO | WO-03/086104 | ‡ | 10/2003 | |
| WO | 2004041251 A1 | | 5/2004 | |
| WO | WO-2004/04125 A1 | ‡ | 5/2004 | ............ A61K 9/5073 |
| WO | 2008017962 A2 | | 2/2008 | |
| WO | WO-2008017962 A2 | ‡ | 2/2008 | ............. A23P 10/30 |
| WO | 2008109806 A2 | | 9/2008 | |
| WO | WO-2008/109806 A2 | ‡ | 9/2008 | ............. C12N 15/87 |
| WO | 2011079279 A2 | | 6/2011 | |
| WO | WO-2011/079279 A2 | ‡ | 6/2011 | .............. A61P 35/00 |

OTHER PUBLICATIONS

Official Action for Mexican Patent Application No. MX/a/2013/003074, translation only.‡
Examination Report for European Patent Application No. 11827375.4, dated Oct. 9, 2017.‡
Notification of Provisional Rejection for Korean Patent Application No. 10-2013-7009508, dated Aug. 1, 2017, with partial translation.‡
Extended European Search Report for European Patent Application No. 11827375.4 dated Sep. 1, 2015.‡
Official Action dated Apr. 12, 2016 in connection with Japanese Patent Application No. 2013-529420 (3 pages).‡
Examination Report for Japanese Patent Application No. 2017-048254 dated Dec. 27, 2017.‡
Examination Report for Canadian Patent Application No. 2,821,504 dated Nov. 30, 2017.‡
Gaihre, B. et al., "Gelatin-coated magnetic iron oxide nanoparticles as carrier system: Drug loading and in vitro drug release study," International Journal of Pharmaceutics 365 (2009) 180-189.‡
Drug Information System, "Dextromethorphan," <http://druginfosys.com/Drug.aspx?drugCode=226&drugName=>, © 2002-2014, p. 1-3.‡
Official Action dated Apr. 12, 2016 in connection with Japanese Patent Application No. 2013-529420.
International Search Report and Written Opinion for International Application No. PCT/US2011/052406, dated Feb. 7, 2012.
Technical Report for Brazilian Patent Application No. 112013006381, dated Nov. 6, 2019.
Examination Report for Indian Patent Application No. 2832/DELNP/2013, dated May 21, 2019.

\* cited by examiner
‡ imported from a related application

MICROENCAPSULATION PROCESS AND PRODUCT

CROSS REFERENCE TO RELATED APPLICATIONS

This application is a continuation of U.S. patent application Ser. No. 13/825,026, filed on Nov. 1, 2013, which claims the benefit of International Application No. PCT/US2011/052406, filed Sep. 20, 2011, which claims the benefit of U.S. Provisional Patent Application No. 61/384,351, filed Sep. 20, 2010, each of which is incorporated herein by reference in its entirety.

FIELD OF THE INVENTION

The present invention relates to a process for forming microcapsules and to the microcapsules produced and method of making and using pharmaceutical formulations using such microcapsules.

BACKGROUND OF THE INVENTION

Microcapsules are small particles of solids, or droplets of liquids, or combinations thereof, inside a thin coating of a material such as gelatin, lipids, starch, cellulosic proteins such as whey proteins, polysaccharides, wax or polyacrylic acids.

The use of microencapsulated compounds has many advantages over the use of unencapsulated compounds. In particular, microencapsulation separates the core material from its environment and provides for taste-masking, controlled release rates, reduced toxicity, and protection against oxidation and moisture, as well as prevention of caking. The release rate of the core material and the diffusion of the core material through the capsule wall can be controlled by varying the wall composition, its thickness and the structure of the walls.

Simple or complex coacervation microencapsulation techniques can be used to make microcapsules. Although these techniques are known, the processes can be long, can involve undesirable solvents, can result in unwanted agglomeration, and can have limitations in controlling microcapsule size.

SUMMARY OF THE INVENTION

The present invention provides for various embodiments of a composition including a core material, having a taste value, and a polymeric coating and methods to manufacture the same. In some embodiments, the composition provides release of a portion of the core material which is taste masked over a time period ranging from 0.5 minute to 2 minutes in the oral cavity and provides modified-release of the remaining core material in a gastrointestinal tract. In some embodiments, the polymeric coating substantially surrounds the core material and includes a cationic polymer and optionally an anionic polymer. In some embodiments, the polymer coating includes a cationic polymer and an anionic polymer. In some embodiments, the polymer coating further includes a crosslinking agent. In some embodiments, the composition has the form of a microcapsule. In some embodiments, the polymeric coating is hydrophilic.

According to the present invention, the polymeric coating has a uniform thickness ranging from 1 µm to 20 µm. In some embodiments, the uniform thickness of the polymeric coating varies over a range from 0.2 µm to 2.0 µm.

According to the present invention, the core material comprises an active pharmaceutical ingredient. In some embodiments, the active pharmaceutical ingredient includes acetaminophen, ibuprofen, dexibuprofen lysinate, naproxen, loperamide dimenhydrinate, doxylamine, dextromethorphan and cholorpheniramine.

In some embodiments, the cationic polymers contained in the polymeric coating include: gelatin type A, gelatin type B, gelatin hydrolysates, gelatin succinylates, ovalbumin, serum albumin, casein, chitin, polyvinylamine, cellulose derivatives, or mixtures thereof.

In some embodiments, the anionic polymers contained in the polymeric coating include a polyphosphates, chitosan, linear silicones, gum arabic, sodium alginate, carrageenan, cellulose acetate phthalate, pectin, carboxymethylcellulose, ethylene maleic anhydride or mixtures thereof. In some such embodiments, the polyphosphates are a mixture of linear polyphosphates of varying chain lengths. In some such embodiments, the polyphosphate mixture is a medium chain polyphosphate and a long chain polyphosphate. In some embodiments, the core material has a water solubility taste threshold and an associated pH of less than or equal to 6 and the polymeric coating has a pH value less than or equal to the associated pH of the water solubility taste threshold. In other embodiments, the core material has a water solubility taste threshold and an associated pH of greater than or equal to 6 and the polymeric coating has a pH value less than or equal to the associated pH of the water solubility taste threshold. In some such embodiments, the water solubility taste threshold ranges from $1\times10^{-4}$ mol/L to $1\times10^{-1}$ mol/L.

In other embodiments, the present invention relates to a pharmaceutical formulation including a composition as described above and further comprising one or more pharmaceutically acceptable ingredients. In some embodiments, pharmaceutically acceptable ingredients may include excipients, binders, lubricants, disintegrating agents, sugar alcohols, colors, flavors and combinations thereof. In some embodiments, the formulation may be compressible at a compression pressure of up to 160 MPa and may retain the composition's taste mask and modified-release properties.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the embodiments set forth herein.

DETAILED DESCRIPTION OF THE INVENTION

Figure 1:
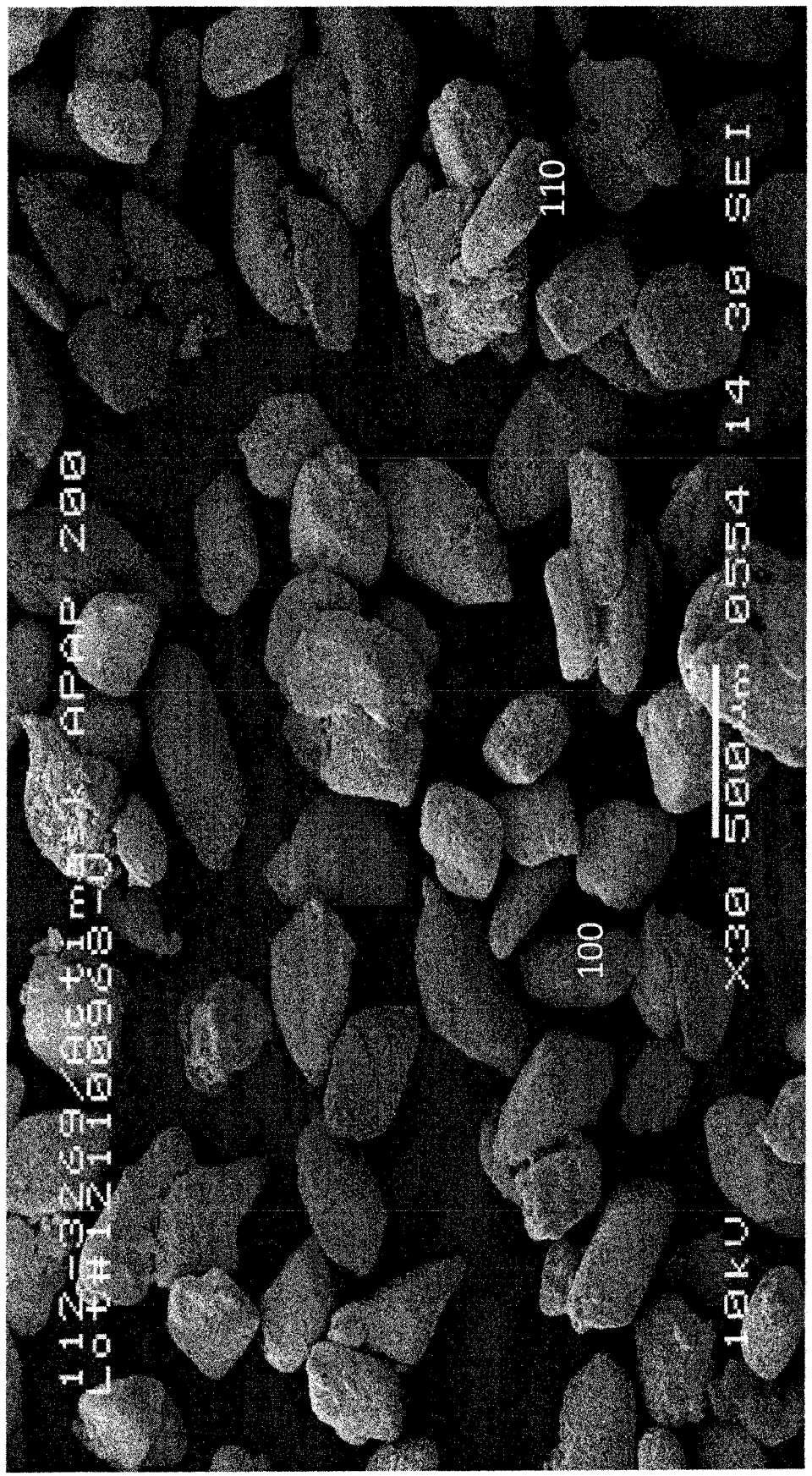
FIG. 1 illustrates a SEM of an exemplary microcapsule composition having taste mask properties and wherein the core material is acetaminophen and the polymeric coating includes gelatin, polyphosphate and transglutimase as described in Example 8.

In certain embodiments, the present invention provides for a composition which taste masks the taste value of a core material and provides modified-release of the core material from the composition.

In some embodiments, the composition includes (i) a core material having a taste value; and (ii) a polymeric coating substantially surrounding the core material, and wherein such composition taste masks the taste value of the core material and modifies the release of the core material from the composition. In some embodiments, the composition may have the form of a microcapsule. In some embodiments, the microcapsules exist as individual microcapsules. In some embodiments, a majority of the microcapsules exist as individual microcapsules with any agglomerates of microcapsules lacking a polymeric coating on the agglomerate exterior surface.

As used herein, taste mask means to modify, mask or reduce the unpleasant taste value of a core material in a subject's oral cavity. The taste value of a core material may include sweetness, bitterness, spicy or hot, sourness, saltiness, and umami each of varying degree.

In one embodiment, taste mask may be determined by a taste panel. An exemplary taste panel may be conducted using a selected number of healthy human volunteers, of either sex and a selected age group, using a standard taste composition. For example in the case of a bitter core material, 6-n-propylthiouracil may be used. Taste threshold for all the volunteers may be determined by making a range of dilutions of the standard taste composition. The non-tasters and super-tasters may be rejected. A selected panel of the volunteers may then test the taste of the composition for a selected time while keeping the composition in the mouth. The selected time may include 0.5-1 minutes; 1-2 minutes, 3 minutes, 4 minutes and 5 minutes. The taste of the composition may be ranked on a scale of perception ranging from 0-5 where 0=good, 1=tasteless, 2=slightly bitter, 3=bitter, 4=very bitter, 5=awful.

In some embodiments, a taste masked composition, according to the present invention, may have a majority of panel rankings ranging from 0 to 2 for up to five minutes in the oral cavity. In some embodiments, a taste masked composition, according to the present invention, may have at least 55% of panel rankings ranging from 0 to 2 for up to five minutes in the oral cavity. In some embodiments, a taste masked composition, according to the present invention, may have at least 60% of panel rankings ranging from 0 to 2 for up to five minutes in the oral cavity. In some embodiments, a taste masked composition, according to the present invention, may have at least 70% of panel rankings ranging from 0 to 2 for up to five minutes in the oral cavity. In some embodiments, a taste masked composition, according to the present invention, may have at least 80% of panel rankings ranging from 0 to 2 for up to five minutes in the oral cavity. In some embodiments, a taste masked composition, according to the present invention, may have at least 90% of panel rankings ranging from 0 to 2 for up to five minutes in the oral cavity. In some embodiments, a taste masked composition, according to the present invention, may have at least 95% of panel rankings ranging from 0 to 2 for up to five minutes in the oral cavity.

In another embodiment, taste mask may be determined by the amount of core material which is released from the composition, according to the present invention, into the oral cavity of a patient, thereby preventing the patient from tasting the drug. In one embodiments, a composition, according to the present invention, which taste masks the taste of the core material may release less than about 40 wt. % of the drug in the oral cavity of the patient, In other embodiments, a composition, according to the present invention, which taste masks the taste of the core material may release: less than about 30 wt. %; less than about 20 wt. %; less than about 10 wt. %; less than about 0.5%; less than about 0.1%; less than about 0.05%; less than about 0.03%; or less than about 0.01% of the drug.

In some embodiments, the core material has a water solubility taste threshold and an associated pH of less than or equal to 6. As used herein, water solubility taste threshold means the molar concentration of the core material in water at which the core material may be perceived. In some embodiments, the core material has a water solubility taste threshold and an associated pH of greater than or equal to 6. In some such embodiments, the associated pH may correspond to the pKa of the core material. The core material water solubility taste threshold may range from $1\times10^{-4}$ mol/L to $1\times10^{-1}$ mol/L.

Figure 4:
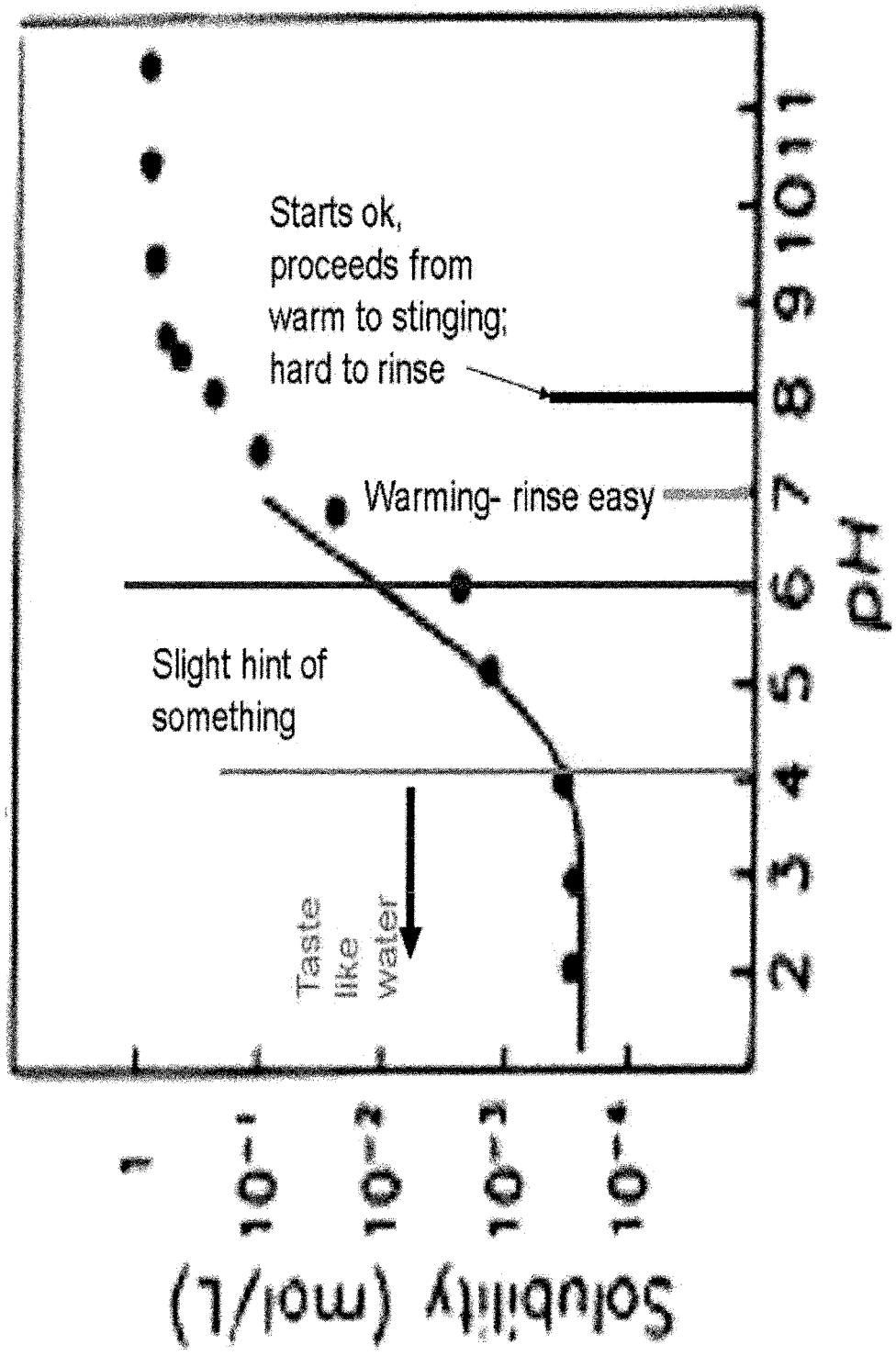
FIG. 4. illustrates the water solubility of uncoated ibuprofen as a function of pH.

For example, FIG. 4. illustrates the water solubility taste threshold versus pH for uncoated ibuprofen. Uncoated ibuprofen's water solubility increases with increasing pH. At a pH of less than 5, uncoated ibuprofen had a water solubility taste threshold of less than $10^{-3}$ and was barely or not perceived according to rankings by a taste panel as described herein.

As used herein, the term "modified-release" includes delay release, sustain release, extend release, prevent release, and/or otherwise prolong the release of a core material into a subject's gastrointestinal tract relative to compositions lacking the various embodiments of polymeric coatings as described herein or relative to compositions having different polymeric coatings from the various embodiments of polymeric coatings as described herein.

According to the present disclosure, the various embodiments of the composition are capable of taste masking the taste value of a core material while also modifying the release of the core material from the composition. In some embodiments, the modified-release of the core material may correspond to a core material release profile which substantially approaches a release profile of the uncoated core material after a predetermined time period in a subject's gastrointestinal track. In some embodiments, the modified-release of the core material may correspond to a core material release profile which substantially approaches a release profile of the uncoated core material after a predetermined time period from being released from the subject's oral cavity.

In some embodiments, the term "substantially approaches" means the dissolution of the polymeric coated core material is at least 90%, preferably 95%, of the dissolution of uncoated core material at predetermined time and conditions set forth herein. In such embodiments, the predetermined time in a subject's gastrointestinal track may be at least: 5 minutes; 20 minutes; 30 minutes; 45 minutes and 60 minutes. In some such embodiments, the polymeric coated core material dissolution and uncoated core material dissolution may be measured in an aqueous solution at 37° C. with a solution at pH 1.2 to 8.

In some other embodiments, "substantially approaches" means the dissolution of at least 90%, preferably 95%, of the polymeric coated core material at a predetermined time and condition as set forth herein. In some such embodiments, the predetermined time in a subject's gastrointestinal track may be at least: 5 minutes; 20 minutes; 30 minutes; 45; or 60 minutes. In some such embodiments, the core material dissolution and uncoated core material dissolution may be measured in an aqueous solution with a phosphate buffer at 37° C. with a solution at pH 1.2 to 8.

In some embodiments, modified-release of the core material from the composition may correspond to dissolution of the core material, at a predetermined time and condition as set forth herein, which is greater than the release of core material from a composition having a cellulose based coating after a predetermined time period in a subject's gastrointestinal track. In such embodiments, the modified-release of the core material may be at least 2 times greater than release of core material from a cellulose-coated material. In other such embodiments, the modified-release of the core material may be at least 3 times greater compared to the release of core material from a cellulose-coated material. In other such embodiments, the modified-release of the core material may be at least 4 times greater compared to the release of core material from a cellulose-coated material. In some such embodiments, the predetermined time in a subject's gastrointestinal track may be at least: 5 minutes; 20 minutes; or 30 minutes. In some such embodiments, the core material dissolution and uncoated core material dissolution may be measured in an aqueous solution with a phosphate buffer at 37° C. with a solution at pH 1.2 to 8.

Core

Any core material that may be encapsulated in a polymeric coating may be used in embodiments of the present invention. In some embodiments, the core is a solid, a hydrophobic liquid or a mixture of a solid and a hydrophobic liquid. Solids include, but are not limited to, active pharmaceutical ingredients (APIs), nutriceuticals, nutritional supplements, vitamins or mixtures thereof. Suitable such APIs include but are not limited to those described in the *Physician's Desk Reference*, 61st ed. Montvale, N.J.: Thomson PDR; 2007, which is incorporated by reference herein in its entirety. Hydrophobic liquids include, but are not limited to, grease, oils or a mixture thereof. Oils include, but are not limited to, fatty acids, triglycerides or mixtures thereof.

In some embodiments, a core material of the present invention may be from about 1 µm to about 500 µm.

In one embodiment, the core material is an active pharmaceutical ingredient. In another embodiment, the core material is a combination of two or more active pharmaceutical ingredients. As used herein, an active pharmaceutical ingredient includes a pharmaceutically acceptable and therapeutically effective amount of the drug, the pharmaceutically acceptable salts, stereoisomers and mixtures of stereoisomers, solvates (including hydrates), polymorphs, and/or esters thereof. Exemplary classes of active pharmaceutical ingredients include, but are not limited to, Analgesics (NSAID); Anti Diarrhea; H2-Antagonistist; Hypertension; Antihistamine/Cold; Anti-cholesterol; Diet; Stimulant; Motion sickness; Sedative; Physcotic; Steroidal; and Anticholinergic. Exemplary active pharmaceutical ingredients include, but are not limited to, acetaminophen; ibuprofen; dexibuprofen lysinate; naproxen; loperamide; famotidine; fanitidine; cimetidine; lisinopril; chlorpheniramine; pseudoephedrine; phenylpropanolamine; diphenhydramine; bromopheniramine; ephedrine; dextromethorphan; phenylepherine; atorvastatin (Lipitor and Torvast); fluvastatin (Lescol); lovastatin (Mevacor, Altocor, Altoprev); pitavastatin (Livalo, Pitava); pravastatin (Pravachol, Selektine, Lipostat); rosuvastatin (Crestor); simvastatin; amphetamines; theophylline; 8-chlortheophylline; dimenhydrinate; phenobarbitol; doxlyamine; codeine; methyldopa; phenyltoloxamine; pheniramine; disulfiram; prednisone; prednisolone; and pilocarpine and combinations thereof. In some embodiments, the active pharmaceutical ingredients include acetaminophen; ibuprofen; dexibuprofen lysinate; naproxen; loperamide; famotidine; fanitidine; cimetidine; lisinopril; dimenhydrinate; doxylamine; dextromethorphan; and cholorpheniramine.

Polymeric Coating

In some embodiments, the polymeric coating includes a cationic polymer and optionally an anionic polymer. In some embodiments, the polymeric coating includes a cationic polymer and an anionic polymer. In some embodiments, the polymeric coating includes a cationic polymer, an anionic polymer and a cross-linking agent.

In some embodiments, the polymeric coating is hydrophilic. In some embodiments, the polymeric coating may have a pH value less than or equal to the associated pH of the core material's water solubility taste threshold.

As used herein, the term "substantially surrounding" means that at least 90% of the core material surface area is surrounded by the polymeric coating.

Figure 2:
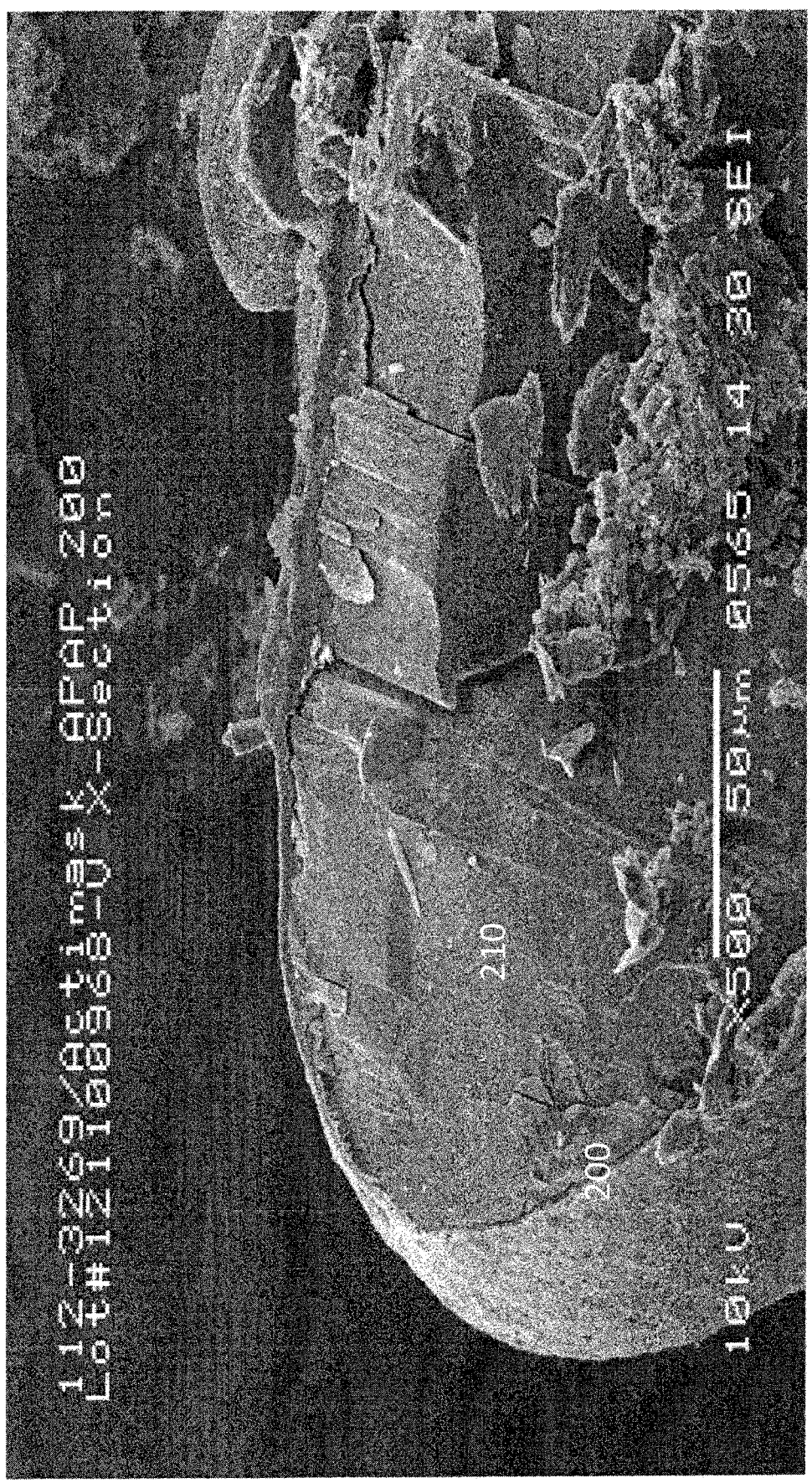
FIG. 2 illustrates a SEM of an exemplary microcapsule composition having taste mask properties and wherein the core material is acetaminophen and the polymeric coating includes gelatin, polyphosphate and transglutimase as described in Example 8.

FIG. 2 illustrates a SEM, at 30× magnification, of an exemplary microcapsule composition having taste mask and modified-release properties and wherein the core material is acetaminophen and the polymeric coating includes gelatin, polyphosphate and transglutimase as described in Example 8. The microcapsule composition is primarily individual particles. As illustrated, any agglomerated microcapsules do not contain a coating over the agglomerate.

Figure 3:
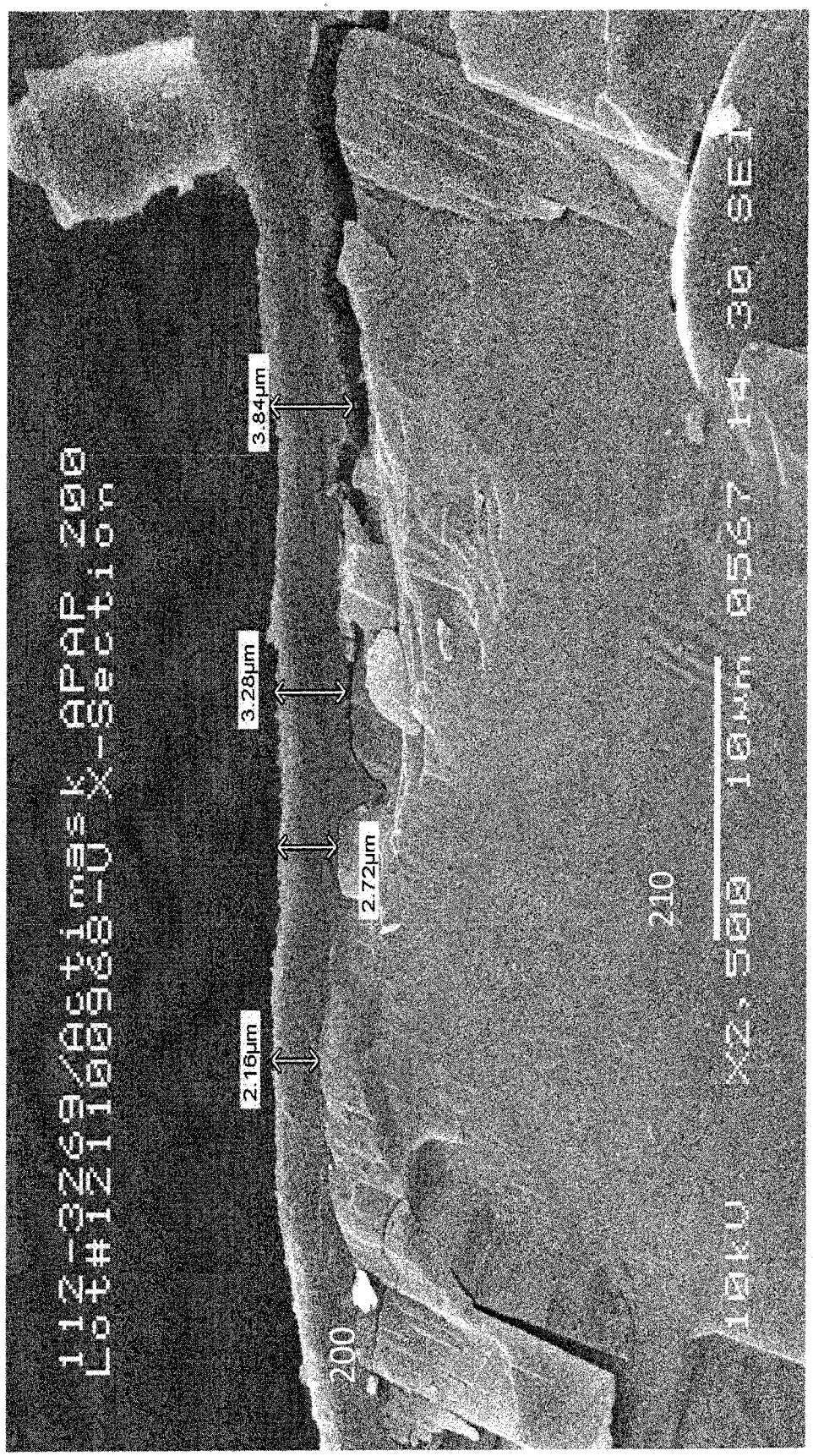
FIG. 3 illustrates a SEM of an exemplary microcapsule composition having taste mask properties and wherein the core material is acetaminophen and the polymeric coating includes gelatin, polyphosphate and transglutimase as described in Example 8. The polymeric coating has a thickness ranging from 2.16 µm to 3.84 µm.

FIG. 3 illustrates a SEM, at 500× magnification of the image in FIG. 2, of an exemplary microcapsule composition having taste mask and modified-release properties and wherein the core material is acetaminophen and the polymeric coating includes gelatin, polyphosphate and transglutimase as described in Example 8. As shown, the polymeric coating 100 substantially surrounds the acetaminophen core material 110.

In some embodiments, the polymeric coating has a uniform thickness ranging from 1 µm to 20 µm. In some embodiments, the polymeric coating has a uniform thickness ranging from 1 µm to 15 µm. In some embodiments, the polymeric coating has a uniform thickness ranging from 1 µm to 10 µm. In some embodiments, the polymeric coating has a uniform thickness ranging from 1 µm to 5 µm. In some embodiments, the polymeric coating has a uniform thickness ranging from 2 µm to 20 µm. In some embodiments, the polymeric coating has a uniform thickness ranging from 2 µm to 15 µm. In some embodiments, the polymeric coating has a uniform thickness ranging from 2 µm to 10 µm. In some embodiments, the polymeric coating has a uniform thickness ranging from 2 µm to 5 µm.

In some embodiments, the uniform thickness of the polymeric coating may have variability. In some embodiments, the uniform polymeric coating thickness may vary over a range from 0.2 µm to 2.0 µm. In some embodiments, the uniform polymeric coating thickness may vary over a range from 0.2 µm to 1.5 µm. In some embodiments, the uniform polymeric coating thickness may vary over a range from 0.2 µm to 1.0 µm. In some embodiments, the uniform polymeric coating thickness may vary over a range from 0.2 µm to 0.7 µm. In some embodiments, the uniform polymeric coating thickness may vary over a range from 0.2 µm to 0.5 µm. In some embodiments, the uniform polymeric coating thickness may vary over a range from 0.5 µm to 1.5 µm. In some embodiments, the uniform polymeric coating thickness may vary over a range from 1.0 µm to 1.5 µm.

FIG. 4 illustrates a SEM, at 2,500× magnification of the image in FIG. 2, of an exemplary microcapsule composition having taste mask and modified-release properties and wherein the core material is acetaminophen and the polymeric coating includes gelatin, polyphosphate and transglutimase as described in Example 8. As shown, the polymeric coating 100 has a thickness ranging from 2.16 µm to ~3.84 µm. The uniform coating thickness varies from 0.56 µm to 1.7 µm.

In some embodiments, the composition, according to the present invention, contains 80 wt. % of core material and 20 wt. % of polymeric coating. In some embodiments, the composition, according to the present invention, contains 85 wt. % of core material and 15 wt. % of polymeric coating. In some embodiments, the composition, according to the present invention, contains 90 wt. % of core material and 10 wt. % of polymeric coating. In some embodiments, the composition, according to the present invention, contains 95 wt. % of core material and 5 wt. % of polymeric coating.

In some embodiments, the cationic polymer may include gelatin type A, gelatin type B, gelatin hydrolysates, gelatin succinylates, ovalbumin, serum albumin, casein, chitin, polyvinylamine, cellulose derivatives, or mixtures thereof. In some embodiments, the cationic polymer may include gelatin type A, gelatin type B, gelatin hydrolysates, gelatin succinylates, or mixtures thereof. In some embodiments, the cationic polymer is gelatin type A.

In some embodiments, the anionic or negatively charged polymer mixture includes a mixture of anionic or negatively charged polymers of varying lengths. In some embodiments, the anionic polymer is a mixture of polyphosphates, chitosan, linear silicones, gum arabic, sodium alginate, carrageenan, cellulose acetate phthalate, pectin, carboxymethylcellulose, ethylene maleic anhydride or mixtures thereof. In other embodiments, the anionic polymer is a mixture of polyphosphates. In some embodiments, the polyphosphates are substantially linear. In some embodiments, the polyphosphates are linear polyphosphates. In some embodiments, the polyphosphates can contain cyclic polyphosphates. In some embodiments, the polyphosphates are a mixture of polyphosphates of varying chain lengths. In some embodiments, the polyphosphates are a mixture of substantially linear polyphosphates of varying chain lengths. In some embodiments, the polyphosphates are a mixture of linear polyphosphates of varying chain lengths. In some embodiments, the polyphosphate mixture is a medium chain polyphosphate and a long chain polyphosphate. In some embodiments, the polyphosphate mixture is a short chain polyphosphate and a long chain polyphosphate. In some embodiments, the polyphosphate mixture is a short chain polyphosphate and a medium chain polyphosphate. In some embodiments, the polyphosphates are from about 1 to about >21 phosphate units in length. In some embodiments, the polyphosphates are from about 3 to >21 phosphate units in length. In some embodiments, the molecular weights of the polyphosphates are from about 137.9 to about 6000. In some embodiments, short chain polyphosphates range from about 3 to about 10 phosphate units in length. In some embodiments, medium chain polyphosphates range from about 11 to about 20 phosphate units in length. In some embodiments, long chain polyphosphates are greater than 20 phosphate units in length. In some embodiments, the short chain polyphosphate is 3 phosphate units in length. In some embodiments, the short chain polyphosphate is 8 phosphate units in length. In some embodiments, the medium chain polyphosphate is 13 phosphate units in length. In some embodiments, the long chain polyphosphate is 21 phosphate units in length. Short chain polyphosphates include, but are not limited to, tripolyphosphate, tetrasodium pyrophosphate (TSPP) and tetrapotassium pyrophosphate (TKPP) (ICL Performance Products, St. Louis, Mo.). Medium chain polyphosphates include, but are not limited to, sodium hexametaphosphate (SHMP) Hexaphos (ICL Performance Products, St. Louis, Mo.). Long chain polyphosphates include, but are not limited to, Glass H (ICL Performance Products, St. Louis, Mo.).

In some embodiments, the ratio of polyphosphates of varying chain lengths is from about 5:95 to about 95:5. In some embodiments, the ratio of a long chain polyphosphate to a medium chain polyphosphate is from about 25:75 to about 40:60. In some embodiments, the ratio of a long chain polyphosphate to a medium chain polyphosphate is 40:60. In some embodiments, the ratio of a long chain polyphosphate to a short chain polyphosphate is from about 25:75 to about 40:60.

In some embodiments, the ratio of cationic polymer:anionic polymer that is used depends on the type of polymers used, but is typically in the range from about 1:1 to about 9:1. In some embodiments, when gelatin type A and a mixture of polyphosphates are used as cationic polymer and anionic polymer respectively, the ratio of cationic polymer:anionic polymer is about 9:1 to 11:1.

In some embodiments, the polymeric coating may include a cross-linker. Cross-linkers may function to reduce the tackiness of the polymer coating and to harden the polymer coating material and thus stabilize the composition. The greater the percent composition of gelatin on the surface, the more effective is the cross-linking. The use of a ratio of polyphosphates of varying chain lengths allows the concentration of gelatin, the film or coating former, to be maximized. Cross-linkers useful in the present invention include, but are not limited to, transglutaminase, glutaraldehyde, formaldehyde, other compounds containing aldehydes, tannic acid, alum, or mixtures thereof. In preferred embodiments, the cross-linker is transglutaminase. When microcapsules are to deliver a biologically active substance to an organism, the cross-linkers are preferably non-toxic or of sufficiently low toxicity. The type and amount of cross-linker used depend on the type of coating material and may be adjusted to provide more or less structural support as needed. For example, when gelatin type A is used in the coating material, transglutaminase may be used in an amount from about 1.5% to about 4.0% of total solids. In some embodiments, transglutaminase may be used in an amount of about 2% of total solids.

Dosage Forms

The various embodiments of the composition, according to the present invention, may be used in a variety of dosage forms including, but not limited to, chewable tablets; swallow tablet; soft chews including tablets and soft gel capsules; orally disintegrating tablet; orally dispersible powders; lozenges; film strips; gums; gels; ointments and creams; tablet inserts (eye, ear, vaginal); suppositories; hard shell capsules; liquid fill capsules; soft gel capsules; liquid suspensions; and sustained release beads. In some embodiments, the dosage form may include chewable tablets; swallow tablet; soft chews including tablets and soft gel capsules; orally disintegrating tablet and orally dispersible powders.

In some embodiments, the dosage form may include a pharmaceutically acceptable ingredient including, but not limited to, excipients, diluents; disintegrants; binders; fillers; bulking agent; organic acid(s); colorants; stabilizers; preservatives; lubricants; glidants/anti-adherants; chelating agents; vehicles; bulking agents; stabilizers; preservatives; tonicity adjusting agents; local anesthetics; pH adjusting agents; antioxidants; osmotic agents; chelating agents; viscosifying agents; wetting agents; emulsifying agents; acids; sugar alcohol; reducing sugars; non-reducing sugars and the like used either alone or in combination thereof. In some embodiments, the pharmaceutically acceptable ingredients may include excipients, binders, lubricants, sugar alcohols, disintegrating agents, colors, flavors and the like used either alone or combinations thereof.

In some embodiments, the composition, according to the present invention, may be used in a compressible dosage form. The term "compressible" means that the composition can be compressed to tablet form on standard tableting machines (including, but not limited to high speed tableting machines) using standard (i.e., without any specially machined, shaped or coated surfaces) punches and dies, without any significant amount of the composition adhering to the punches and dies by applying compressive pressure to the composition. In some embodiments, the compression pressure ranges from 60 Mpa to 160 MP. In some embodiments, the compression force ranges from 80 Mpa to 150 Mpa. In some embodiments, the compression pressure is up to 160 Mpa.

In some embodiments, a compressible composition includes a plurality of microcapsules, of the various embodiments of compositions described herein, and retains the capability of taste mask and modified-release of the core material after being subjected to compression pressure. In some embodiments, the compression pressure ranges from 60 Mpa to 160 MP. In some embodiments, the compression force ranges from 80 Mpa to 150 Mpa. In some embodiments, the compression pressure is up to 160 Mpa.

The composition, according to the present invention, may be produced by a variety of processes including microencapsulation, coacervation, multinozzle spray systems, hot melt granulation, fluid bed top spray coating, fluid bed tangential spray coating, Wurster coating and spray drying. In some embodiments, the composition may be produced via coacervation. In some embodiments, the composition may be produced via multinozzle spray systems. In some embodiments, the composition may be produced via hot melt granulation. In some embodiments, the composition may be produced via fluid bed top spray coating. In some embodiments, the composition may be produced via fluid bed tangential spray coating. In some embodiments, the composition may be produced via Wurster coating. In some embodiments, the composition may be produced via spray drying.

Process

In some embodiments, the process of the present invention is intended to produce individual coated particles or microcapsules. In some embodiments, the process of the present invention is intended to produce individual coated particles or microcapsules, and not agglomerates.

In some embodiments, the process of the present invention shortens the encapsulation process. In another embodiment, process time is controlled by rate of temperature dropping with droplet size controlled primarily by the ratio of polyphosphates. In other embodiments, process time is shortened by creating small coating particle droplets but more of them. As the polymeric material is brought out of solution by either temperature or pH it forms coating droplets or films. Droplet size is normally controlled by slowing the rate of polymer leaving the solution. Process time is shortened by allowing the droplet density (number of droplets formed per volume) to rise but still keeping the droplet size the same. In the typical coacervation process, larger coating droplets are prevented and the issues of them adhering less to the core and more to each other to form a gel in the solution by keeping the rate of the polymer exiting the solution slower.

In coacervation processes, agitation rate is focused on the prevention of the formation of agglomerates versus also controlling coating droplet size. In some embodiments, the process of the present invention comprises the use of agitation rates which are slower than rates typically needed to maintain coating particle droplet size. The use of slower agitation rates improves droplet or film adhesion to coating surfaces thereby reducing particle coating erosion. Coating particles adhere and break off the core due to their size (smaller coating particles are best), their adhesive strength, and the rate of fluid flow (slower agitation rates are best). The process of the present invention allows the agitation rate to be slower as the coating particle size is controlled by polymer length ratio, thereby shortening process time.

Typically droplet size control in current technology is focused mainly on rate of temperature drop. Slow enough so the droplets do not get too large. The rate of droplet creation is the target of the current technology to control droplet size formed and not the rate of coating (droplet placement). Small droplets will apply to the surface as a coating with less coated particle agglomeration and be less prone to agitation/ erosion due to stirring rate.

With the use of a ratio of polyphosphates of varying chain lengths according to the present invention, temperature drop can be tied primarily to the rate of coating (droplet creation) and less to control of droplet size. Droplet size is controlled primarily by the polyphosphate selection in the invention. As temperature drops more small droplets are created versus fewer larger droplets and if the process is pushed faster, faster rate of temperature drop, control based on polyphosphate chain length can maintain the smaller droplets versus having larger droplets created.

In some embodiments, the process of the invention allows pH to be used more for matching of core surface-coating particle compatibility versus as primary aide along with temperature to maintain coating particle droplet size. This allows for a greater variety of cores to be coated and improves adhesion of coating particle to core and decreases process time.

In some embodiments, the process according to the present invention comprises the steps of dispersing a solid core material in a solution of a cationic polymer at a starting temperature, adding anionic or negatively charged polymer mixture either as pre-dissolve and/or solid ingredients to the core/cationic polymer mixture, adjusting pH of mixture, cooling the mixture at a controlled rate, optionally adding cross-linker to mixture, optionally centrifuging or filtering mixture to remove water, and then drying mixture. The various embodiments of core material, cationic polymer and negatively charged polymer are discussed above herein.

In some embodiments, the core can be dispersed or added to the cationic polymer solution or suspension as a liquid and in process milled into droplets or into an emulsion.

In some embodiments, the starting temperature is from about 40° C. to about 80° C. In some embodiments, the starting temperature is from about 45° C. to about 80° C. In some embodiments, the starting temperature is from about 45° C. to about 75° C. In some embodiments, the starting temperature is from about 45° C. to about 70° C. In other embodiments, the starting temperature is from about 50° C. to about 70° C. In preferred embodiments, the starting temperature is from about 50° C. to about 60° C.

In some embodiments, the adjustment of pH of the mixture is in the range of about 4.5 to about 7.0. In some embodiments, the adjustment of pH of the mixture is in the range of about 4.5 to about 6.5. In some embodiments, the adjustment of pH of the mixture is in the range of about 4.5 to about 6.0. In some embodiments, the adjustment of pH of the mixture is in the range of about 4.5 to about 5.5. In some embodiments, the adjustment of pH of the mixture is in the range of about 4.5 to about 5.0. In other embodiments, the adjustment of pH of mixture is in the range of about 4.6 to about 4.9. In other embodiments, the adjustment of pH of mixture is in the range of about 4.7 to about 4.8. In some embodiments, the adjustment of pH of mixture is to 4.5. In some embodiments, the adjustment of pH of mixture is to 4.6. In some embodiments, the adjustment of pH of mixture is to 4.7. In some embodiments, the adjustment of pH of mixture is to 4.8. In some embodiments, the adjustment of pH of mixture is to 4.9. In some embodiments, the adjustment of pH of mixture is to 5.0.

In some embodiments, the mixture is cooled to a temperature in the range from about 25° C. to about 2° C. In some embodiments, the mixture is cooled to a temperature in the range from about 20° C. to about 5° C. In some embodiments, the mixture is cooled to a temperature in the range from about 15° C. to about 8° C. In other embodiments, the mixture is cooled to a temperature in the range from about 12° C. to about 8° C. In other embodiments, the mixture is cooled to a temperature in the range from about 10° C. to about 5° C. In more preferred embodiments, the mixture is cooled to 10° C. In a preferred embodiment, the mixture is cooled to <10° C. In some embodiments, the mixture is cooled at a rate from about 5° C./10 min to about 0.1° C./10 min. In some embodiments, the mixture is cooled to 10° C. at a rate of 5° C./10 minutes. In some embodiments, the mixture is cooled to <10° C. at a rate of 5° C./10 minutes. In other embodiments, the mixture is cooled to 10° C. at a rate of <1° C./10 minutes. In other embodiments, the mixture is cooled to <100° C. at a rate of <1° C./10 minutes.

In some of the process embodiments herein, I use of a single linear medium or short chain polyphosphate in combination with gelatin is in a 9:1 gelatin to polyphosphate ratio results in adequate coating of the core material, however the gelatin does not come out of solution in total, thus the coating is not consistent and not reproducible. Increasing the ratio to higher levels of medium chain polyphosphates decreases the amount of gelatin at the film or coating surface for cross-linking and hardening of the final surface. The use of a single long chain polyphosphate in combination with gelatin results in large droplets, a greater tendency to form a gel and a greater amount of gelatin exiting the solution for a given temperature. The use of a mixture of long and medium chain linear polyphosphates in combination with gelatin results in the gelatin coming out of solution, based on polyphosphate long chain content, and coating the core material consistently with less gel formation and thus a more reproducible coating process based on polyphosphate medium chain amount present.

In some embodiments, the weight percentage ratio of the cationic and anionic polymers may also affect the formation of complex coacervates. In some embodiments, the weight percentage ratio of cationic polymer to anionic polymer ranges from 20:1 to 8:1. In some embodiments, the weight percentage ratio of cationic polymer to anionic polymer ranges from 15:1 to 8:1. In some embodiments, the weight percentage ratio of cationic polymer to anionic polymer ranges from 10:1 to 8:1.

In some embodiments, the concentration of the cationic and anionic polymers may also affect the formation of complex coacervates. In some embodiments, the concentration of the cationic polymer is from about 0.90% to about 1.1%. In a more preferred embodiment, the concentration of the cationic polymer is about 1%. In some embodiments, the concentration of the anionic polymer is from about 0.09% to about 0.11%. In a more preferred embodiment, the concentration of the anionic polymer is about 0.10%. In some embodiments, the total concentration of the cationic and anionic polymers is from about 0.99% to about 1.21%. In a preferred embodiment the total concentration of the cationic and anionic polymers is about 1.10%.

In some embodiments, the agitation rate or mixing speed used to keep the coating droplets or film and the core particle in suspension and to prevent the formation of a gel (coating droplets adhering to one another) is from about 100 rpm to about 1500 rpm. In some embodiments the mixing speed is from about 300 rpm to about 1000 rpm. Mixing speed or agitation rate depend upon the type of equipment being used. Any suitable agitators or mixing equipment may be used in the present invention as long as a suspension of the core material is able to be maintained.

In some embodiments, the resultant microcapsules are dried in fluid bed dryer. In some embodiments, the resultant microcapsules are dried in fluid bed dryer at a temperature of about 35° C. to about 70° C. In preferred embodiments, the resultant microcapsules are dried in fluid bed dryer at a temperature of 40° C. In other embodiments, the resultant microcapsules are dried in tray drying oven. In other embodiments, the resultant microcapsules are dried in tray drying oven at a temperature of about 35° C. to about 60° C. In preferred embodiments, the resultant microcapsules are dried in a tray drying oven at a temperature of 40° C. In some embodiments, the resultant microcapsules are dried in a vacuum dryer. In some embodiments, the resultant microcapsules are dried in a vacuum dryer at a jacket temperature of about 25° C. to about 80° C. In some embodiments, the resultant microcapsules are dried in a vacuum dryer at a jacket temperature of about 25° C. to about 80° C. with partial vacuum. In some embodiments, the resultant microcapsules are dried in a vacuum dryer at a jacket temperature of about 25° C. to about 80° C. with full vacuum. In preferred embodiments, the resultant microcapsules are dried in a vacuum dryer at a jacket temperature of about 60° C. with full vacuum.

In some embodiments, optional additives or processing aids may be incorporated into the microcapsules including, but not limited to, de-agglomeration agents, i.e., agents effective to reduce microcapsule aggregation (e.g., colloidal silica such as that available as Syloid®), colorants (e.g., titanium dioxide, dyes suitable for food such as those known as F.D. & C. dyes, etc.), pH adjusters, buffering agents and/or their salts (e.g., phosphoric acid, acetic acid, citric acid, etc.), stabilizers (e.g., butylated hydroxyanisole (BHA) and butylated hydroxytoluene (BHT), sodium sulfite, etc.), flavoring and/or sweetening agents.

In some embodiments, the process according to the present invention comprises the steps of:
a) adding a core material in a solution of a cationic polymer at a starting temperature and adjusting agitation rate to suspend core material,
b) adding anionic polymer mixture and dissolving in solution,
c) adjusting pH of mixture to charge the cationic polymer,
d) cooling the mixture at a controlled rate, and optionally adjusting agitation rate to control agglomeration,
e) optionally adding cross-linker to mixture,
f) optionally centrifuging or filtering the mixture to remove water, and
g) drying mixture, wherein the anionic polymer mixture comprises anionic polymers of varying lengths. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at a starting temperature and adjusting agitation rate to suspend core material,
b) adding anionic polymer mixture and dissolving in solution,
c) adjusting pH of mixture to charge the cationic polymer,
d) cooling the mixture at a controlled rate, and optionally adjusting agitation rate to control agglomeration,
e) optionally adding cross-linker to mixture,
f) optionally centrifuging or filtering the mixture to remove water, and
g) drying mixture.

wherein the anionic polymer mixture comprises polyphosphates of varying chain lengths. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at a starting temperature and adjusting agitation rate to suspend core material,
b) adding anionic polymer mixture and dissolving in solution,
c) adjusting pH of mixture to charge the cationic polymer,
d) cooling the mixture at a controlled rate, and optionally adjusting agitation rate to control agglomeration,
e) optionally adding cross-linker to mixture,
f) optionally centrifuging or filtering the mixture to remove water, and
g) drying mixture, wherein the anionic polymer mixture comprises medium and long chain polyphosphates. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at a starting temperature and adjusting agitation rate to suspend core material,
b) adding anionic polymer mixture and dissolving in solution,
c) adjusting pH of mixture to charge the cationic polymer,
d) cooling the mixture at a controlled rate, and optionally adjusting agitation rate to control agglomeration,
e) optionally adding cross-linker to mixture,
f) optionally centrifuging or filtering the mixture to remove water, and
g) drying mixture, wherein the anionic polymer mixture comprises medium and long chain polyphosphates in a ratio of 60:40, respectively. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at a starting temperature and adjusting agitation rate to suspend core material,
b) adding anionic polymer mixture and dissolving in solution,
c) adjusting pH of mixture to charge the cationic polymer,
d) cooling the mixture at a controlled rate, and optionally adjusting agitation rate to control agglomeration,
e) optionally adding cross-linker to mixture,
f) optionally centrifuging or filtering the mixture to remove water, and
g) drying mixture, wherein the anionic polymer mixture comprises short and long chain polyphosphates. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at a starting temperature and adjusting agitation rate to suspend core material,
b) adding anionic polymer mixture and dissolving in solution,
c) adjusting pH of mixture to charge the cationic polymer,
d) cooling the mixture at a controlled rate, and optionally adjusting agitation rate to control agglomeration,
e) optionally adding cross-linker to mixture,
f) optionally centrifuging or filtering the mixture to remove water, and
g) drying mixture, wherein the anionic polymer mixture comprises short and medium chain polyphosphates. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at about 45° C. to about 80° C. and adjusting agitation rate to suspend core material,
b) adding anionic polymer mixture and dissolving in solution,
c) adjusting pH of mixture to about 4.5 to about 5.0 to charge the cationic polymer,
d) cooling the mixture at a controlled rate to about 20° C. to about 2° C., and optionally adjusting agitation rate to control agglomeration,
e) optionally adding cross-linker to mixture,
f) optionally centrifuging or filtering the mixture to remove water, and
g) drying mixture, wherein the anionic polymer mixture comprises anionic polymers of varying lengths. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at about 50° C. to about 60° C. and adjusting agitation rate to suspend core material,
b) adding anionic polymer mixture and dissolving in solution,
c) adjusting pH of mixture to about 4.5 to about 4.8 to charge the cationic polymer,
d) cooling the mixture at a controlled rate to about 12° C. to about 8° C., and optionally adjusting agitation rate to control agglomeration,
e) optionally adding cross-linker to mixture.
f) optionally centrifuging or filtering the mixture to remove water, and
g) drying mixture, wherein the anionic polymer mixture comprises anionic polymers of varying lengths. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at about 50° C. and adjusting agitation rate to suspend core material,
b) adding anionic polymer mixture and dissolving in solution,
c) adjusting pH of mixture to 4.8 to charge the cationic polymer,
d) cooling the mixture at a controlled rate to 10° C., and optionally adjusting agitation rate to control agglomeration,
e) optionally adding cross-linker to mixture,
f) optionally centrifuging or filtering the mixture to remove water, and
g) drying mixture.

wherein the anionic polymer mixture comprises anionic polymers of varying lengths. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at about 50° C. and adjusting agitation rate to suspend core material,
b) adding anionic polymer mixture and dissolving in solution,
c) adjusting pH of mixture to 4.8 to charge the cationic polymer,
d) cooling the mixture to 10° C. at a rate of about 5° C./10 min to about 0.1° C./10 min, and optionally adjusting agitation rate to control agglomeration,
e) optionally adding cross-linker to mixture,
f) optionally centrifuging or filtering the mixture to remove water, and
g) drying mixture, wherein the anionic polymer mixture comprises anionic polymers of varying lengths. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at about 50° C. and adjusting agitation rate to suspend core material,
b) adding anionic polymer mixture and dissolving in solution, c) adjusting pH of mixture to 4.8 to charge the cationic polymer,
d) cooling the mixture to 10° C. at a rate of 1° C./10 min, and optionally adjusting agitation rate to control agglomeration,
e) optionally adding cross-linker to mixture,
f) optionally centrifuging or filtering mixture to remove water, and
g) drying mixture, wherein the anionic polymer mixture comprises anionic polymers of varying lengths. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at about 50° C. and adjusting agitation rate to suspend core material,
b) adding anionic polymer mixture and dissolving in solution,
c) adjusting pH of mixture to 4.8 to charge the cationic polymer,
d) cooling the mixture to 10° C. at a rate of 1° C. per 10 min, and optionally adjusting agitation rate to control agglomeration,
e) optionally adding cross-linker to mixture,
f) optionally centrifuging or filtering mixture to remove water, and
g) drying mixture, wherein the anionic polymer mixture comprises medium and long chain polyphosphates. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at about 50° C. and adjusting agitation rate to suspend core material,
b) adding anionic polymer mixture and dissolving in solution,
c) adjusting pH of mixture to 4.8 to charge the cationic polymer,
d) cooling the mixture to 10° C. at a rate of 1° C. per 10 min, and optionally adjusting agitation rate to control agglomeration,
e) optionally adding cross-linker to mixture,
f) optionally centrifuging or filtering mixture to remove water, and
g) drying mixture, wherein the anionic polymer mixture comprises a combination of medium and long chain polyphosphates in a ratio of 60:40. In some such embodiments, the solution is an aqueous solution. In some other such embodiments, the solution is a water/hydrocarbon mixture.

In some embodiments, the process according to the present invention comprises the steps of:
a) adding a core material in a solution of a cationic polymer at about 50° C. and adjusting agitation rate to suspend core material,
b) adding anionic polymer mixture and dissolving in solution,
c) adjusting pH of mixture to 4.8 to charge the cationic polymer,
d) cooling the mixture to 10° C. at a rate of 1° C./10 min, and optionally adjusting agitation rate to control agglomeration,
e) optionally adding cross-linker to mixture, f) optionally centrifuging or filtering mixture to remove water, and
g) drying mixture, wherein the anionic polymer mixture comprises short and long chain polyphosphates.

In some embodiments, the process according to the present invention comprises the steps of:
a) adding a core material in a solution of a cationic polymer at about 50° C. and adjusting agitation rate to suspend core material,
b) adding anionic polymer mixture and dissolving in solution,
c) adjusting pH of mixture to 4.8 to charge the cationic polymer,
d) cooling the mixture to 10° C. at a rate of 1° C./10 min, and optionally adjusting agitation rate to control agglomeration,
e) optionally adding cross-linker to mixture,
f) optionally centrifuging or filtering mixture to remove water, and
g) drying mixture, wherein the anionic polymer mixture comprises short and medium chain polyphosphates. In some such embodiments, the solution is an aqueous solution. In some other such embodiments, the solution is a water/hydrocarbon mixture.

In some embodiments, the process according to the present invention comprises the steps of:
a) adding a core material in a solution of gelatin at about 50° C. and adjusting agitation rate to suspend core material,
b) adding a polyphosphate mixture and dissolving in solution,
c) adjusting pH of mixture to 4.8 to charge the gelatin,
d) cooling the mixture to 10° C. at a rate of 1° C./10 min, and optionally adjusting agitation rate to control agglomeration,
e) optionally adding cross-linker to mixture,
f) optionally centrifuging or filtering mixture to remove water, and
g) drying mixture, wherein the polyphosphate mixture comprises polyphosphates of varying chain lengths. In some such embodiments, the solution is an aqueous solution. In some other such embodiments, the solution is a water/hydrocarbon mixture.

In some embodiments, the process according to the present invention comprises the steps of:
a) adding a core material in a solution of gelatin at about 50° C. and adjusting agitation rate to suspend core material,
b) adding a polyphosphate mixture and dissolving in solution,
c) adjusting pH of mixture to 4.8 to charge the gelatin,
d) cooling the mixture to 10° C. at a rate of 1° C./10 min, and optionally adjusting agitation rate to control agglomeration,
e) optionally adding cross-linker to mixture,
f) optionally centrifuging or filtering mixture to remove water, and
g) drying mixture, wherein the polyphosphate mixture comprises medium and long chain polyphosphates. In some such embodiments, the solution is an aqueous solution. In some other such embodiments, the solution is a water/hydrocarbon mixture.

In some embodiments, the process according to the present invention comprises the steps of:
a) adding a core material in a solution of gelatin at about 50° C. and adjusting agitation rate to suspend core material,
b) adding a polyphosphate mixture and dissolving in solution,
c) adjusting pH of mixture to 4.8 to charge the gelatin,
d) cooling the mixture to 10° C. at a rate of 1° C./10 min, and optionally adjusting agitation rate to control agglomeration,
e) optionally adding cross-linker to mixture,
f) optionally centrifuging or filtering mixture to remove water, and
g) drying mixture, wherein the polyphosphate mixture comprises medium and long chain polyphosphates in a ratio of 60:40. In some such embodiments, the solution is an aqueous solution. In some other such embodiments, the solution is a water/hydrocarbon mixture.

In some embodiments, the process according to the present invention comprises the steps of:
a) adding a core material in a solution of gelatin at about 50° C. and adjusting agitation rate to suspend core material,
b) adding a polyphosphate mixture and dissolving in solution,
c) adjusting pH of mixture to 4.8 to charge the gelatin,
d) cooling the mixture to 10° C. at a rate of 1° C./10 min, and optionally adjusting agitation rate to control agglomeration,
e) optionally adding cross-linker to mixture,
f) optionally centrifuging or filtering mixture to remove water, and
g) drying mixture, wherein the polyphosphate mixture comprises short and long chain polyphosphates. In some such embodiments, the solution is an aqueous solution. In some other such embodiments, the solution is a water/hydrocarbon mixture.

In some embodiments, the process according to the present invention comprises the steps of:
a) adding a core material in a solution of gelatin at about 50° C. and adjusting agitation rate to suspend core material,
b) adding a polyphosphate mixture and dissolving in solution,
c) adjusting pH of mixture to 4.8 to charge the gelatin,
d) cooling the mixture to 10° C. at a rate of 1° C./10 min, and optionally adjusting agitation rate to control agglomeration,
c) optionally adding cross-linker to mixture,
f) optionally centrifuging or filtering mixture to remove water, and
g) drying mixture, wherein the polyphosphate mixture comprises short and medium chain polyphosphates. In some such embodiments, the solution is an aqueous solution. In some other such embodiments, the solution is a water/hydrocarbon mixture.

In some embodiments, the process according to the present invention comprises the steps of:
a) melting a core material in a solution of cationic polymer at about 50° C. or higher and adjusting agitation rate to control melt particle size and maintaining separation of core material,
b) adding anionic polymer mixture and dissolving in solution,
c) cooling the mixture to re-solidify the core or coating the core as a liquid,
d) adjusting pH of mixture to charge the cationic polymer, e) cooling the mixture at a controlled rate, and optionally adjusting agitation rate to control agglomeration,
f) optionally adding cross-linker to mixture,
g) optionally centrifuging or filtering mixture to remove water, and
h) drying mixture wherein the anionic polymer mixture comprises anionic polymers of varying lengths. In some such embodiments, the solution is an aqueous solution. In some other such embodiments, the solution is a water/hydrocarbon mixture.

In some embodiments, the process according to the present invention comprises the steps of:
a) melting a core material in a solution of cationic polymer at about 50° C. or higher,
b) adding anionic polymer mixture and dissolving in solution,
c) cooling the mixture to re-solidify the core or coating the core as a liquid,
d) adjusting pH of mixture to charge to cationic polymer,
e) cooling the mixture at a controlled rate, and optionally adjusting agitation rate to control agglomeration,
f) optionally adding cross-linker to mixture,
g) optionally centrifuging or filtering mixture to remove water, and
h) drying mixture wherein the anionic polymer mixture comprises polyphosphates of varying chain lengths. In some such embodiments, the solution is an aqueous solution. In some other such embodiments, the solution is a water/hydrocarbon mixture.

In some embodiments, the process according to the present invention comprises the steps of:
a) melting the core material in a solution of gelatin at about 50° C. or higher,
b) adding anionic polymer mixture and dissolving in solution,
c) cooling the mixture to re-solidify the core or coating the core as a liquid,
d) adjusting pH of mixture to charge the gelatin,
e) cooling the mixture at a controlled rate, and optionally adjusting agitation rate to control agglomeration,
f) optionally adding cross-linker to mixture,
g) optionally centrifuging or filtering mixture to remove water, and
h) drying mixture wherein the anionic polymer mixture comprises anionic polymers of varying lengths. In some such embodiments, the solution is an aqueous solution. In some other such embodiments, the solution is a water/hydrocarbon mixture.

In some embodiments, the process according to the present invention comprises the steps of:
a) melting the core material in a solution of gelatin at about 50° C. or higher,
b) adding polyphosphate mixture and dissolving in solution,
c) cooling the mixture to re-solidify the core or coating the core as a liquid,
d) adjusting pH of mixture to charge the gelatin,
e) cooling the mixture at a controlled rate, and optionally adjusting agitation rate to control agglomeration,
f) optionally adding cross-linker to mixture,
g) optionally centrifuging or filtering mixture to remove water, and
h) drying mixture wherein the polyphosphate mixture comprises polyphosphates of varying chain lengths. In some such embodiments, the solution is an aqueous solution. In some other such embodiments, the solution is a water/hydrocarbon mixture.

In some embodiments, the process according to the present invention comprises the steps of:
a) melting the core material in a solution of gelatin at about 50° C. or higher,
b) adding polyphosphate mixture and dissolving in solution,
c) cooling the mixture to re-solidify the core or coating the core as a liquid,
d) adjusting pH of mixture to 4.8 to charge the gelatin,
e) cooling the mixture to 10° C. at a rate of 1° C. per 10 min, and optionally adjusting agitation rate to control agglomeration,
f) optionally adding cross-linker to mixture,
g) optionally centrifuging or filtering mixture to remove water, and
h) drying mixture wherein the polyphosphate mixture comprises medium and long chain polyphosphates. In some such embodiments, the solution is an aqueous solution. In some other such embodiments, the solution is a water/hydrocarbon mixture.

In some embodiments, the process according to the present invention comprises the steps of:
a) melting the core material in a solution of gelatin at about 50° C. or higher,
b) adding polyphosphate mixture and dissolving in solution,
c) cooling the mixture to re-solidify the core or coating the core as a liquid,
d) adjusting pH of mixture to 4.8 to charge the gelatin,
e) cooling the mixture to 10° C. at a rate of 1° C. per 10 min, and optionally adjusting agitation rate to control agglomeration,
f) optionally adding cross-linker to mixture,
g) optionally centrifuging or filtering mixture to remove water, and
h) drying mixture wherein the polyphosphate mixture comprises short and long chain polyphosphates. In some such embodiments, the solution is an aqueous solution. In some other such embodiments, the solution is a water/hydrocarbon mixture.

In some embodiments, the process according to the present invention comprises the steps of:
a) melting the core material in a solution of gelatin at about 50° C. or higher,
b) adding polyphosphate mixture and dissolving in solution,
c) cooling the mixture to re-solidify the core or coating the core as a liquid,
d) adjusting pH of mixture to 4.8 to charge the gelatin,
e) cooling the mixture to 10° C. at a rate of 1° C. per 10 min, and optionally adjusting agitation rate to control agglomeration,
f) optionally adding cross-linker to mixture,
g) optionally centrifuging or filtering mixture to remove water, and
h) drying mixture wherein the polyphosphate mixture comprises short and medium chain polyphosphates. In some such embodiments, the solution is an aqueous solution. In some other such embodiments, the solution is a water/hydrocarbon mixture.

Microcapsule

In some embodiments of the present invention, a microcapsule composition comprises microcapsules of a core material in a coacervated polymer material comprising a cationic polymer and an anionic polymer mixture, wherein said anionic polymer mixture comprises anionic polymers of varying lengths. In some embodiments, a microcapsule composition comprises microcapsules of a core material in a coacervated polymer material, which comprises a cationic polymer and a polyphosphate mixture comprising polyphosphates of varying chain lengths. In other embodiments, a microcapsule composition comprises microcapsules of a core material in a coacervated polymer material, which comprises a cationic polymer and a polyphosphate mixture comprising medium and long chain polyphosphates. In other embodiments, a microcapsule composition comprises microcapsules of a core material in a coacervated polymer material, which comprises a cationic polymer and a polyphosphate mixture comprising short and long chain polyphosphates. In other embodiments, a microcapsule composition comprises microcapsules of a core material in a coacervated polymer material, which comprises a cationic polymer and a polyphosphate mixture comprising short and medium chain polyphosphates. In some embodiments, a microcapsule composition comprises microcapsules of a core material in a coacervated polymer material, which comprises gelatin and an anionic polymer mixture comprising anionic polymers of varying lengths. In some embodiments, a microcapsule composition comprises microcapsules of a core material in a coacervated polymer material, which comprises gelatin and a polyphosphate mixture comprising polyphosphates of varying chain lengths. In some embodiments, a microcapsule composition comprises microcapsules of a core material in a coacervated polymer material, which comprises gelatin and a polyphosphate mixture comprising medium and long chain polyphosphates. In some embodiments, a microcapsule composition comprises microcapsules of a core material in a coacervated polymer material, which comprises gelatin and a polyphosphate mixture comprising short and medium chain polyphosphates. In some embodiments, a microcapsule composition comprises microcapsules of a core material in a coacervated polymer material, which comprises gelatin and a polyphosphate mixture comprising short and long chain polyphosphates.

In some embodiments of the present invention, a microcapsule composition comprises microcapsules of a core material in a coacervated polymer material comprising a cationic polymer and an anionic polymer mixture, wherein said anionic polymer mixture comprises anionic polymers of varying lengths and wherein said microcapsule composition has increased dissolution rate. In some embodiments, a microcapsule composition comprises microcapsules of a core material in a coacervated polymer material, which comprises a cationic polymer and a polyphosphate mixture comprising polyphosphates of varying chain lengths, wherein said microcapsule composition has increased dissolution rate. In other embodiments, a microcapsule composition comprises microcapsules of a core material in a coacervated polymer material, which comprises a cationic polymer and a polyphosphate mixture comprising medium and long chain polyphosphates, wherein said microcapsule composition has increased dissolution rate. In other embodiments, a microcapsule composition comprises microcapsules of a core material in a coacervated polymer material, which comprises a cationic polymer and a polyphosphate mixture comprising short and long chain polyphosphates, wherein said microcapsule composition has increased dissolution rate. In other embodiments, a microcapsule composition comprises microcapsules of a core material in a coacervated polymer material, which comprises a cationic polymer and a polyphosphate mixture comprising short and medium chain polyphosphates, wherein said microcapsule composition has increased dissolution rate. In some embodiments, a microcapsule composition comprises microcapsules of a core material in a coacervated polymer material, which comprises gelatin and an anionic polymer mixture comprising anionic polymers of varying lengths, wherein said microcapsule composition has increased dissolution rate. In some embodiments, a microcapsule composition comprises microcapsules of a core material in a coacervated polymer material, which comprises gelatin and a polyphosphate mixture comprising polyphosphates of varying chain lengths, wherein said microcapsule composition has increased dissolution rate. In some embodiments, a microcapsule composition comprises microcapsules of a core material in a coacervated polymer material, which comprises gelatin and a polyphosphate mixture comprising medium and long chain polyphosphates, wherein said microcapsule composition has increased dissolution rate. In some embodiments, a microcapsule composition comprises microcapsules of a core material in a coacervated polymer material, which comprises gelatin and a polyphosphate mixture comprising short and medium chain polyphosphates, wherein said microcapsule composition has increased dissolution rate. In some embodiments, a microcapsule composition comprises microcapsules of a core material in a coacervated polymer material, which comprises gelatin and a polyphosphate mixture comprising short and long chain polyphosphates, wherein said microcapsule composition has increased dissolution rate. In each of the above embodiments, the increased dissolution rate is relative to a prior art microcapsule composition including prior art microcapsule compositions having cellulose based coatings.

In some embodiments of the present invention, a microcapsule composition comprises microcapsules of an active pharmaceutical ingredient in a coacervated polymer material comprising a cationic polymer and an anionic polymer mixture, wherein said anionic polymer mixture comprises anionic polymers of varying lengths and wherein said active pharmaceutical ingredient has increased dissolution rate. In some embodiments, a microcapsule composition comprises microcapsules of an active pharmaceutical ingredient in a coacervated polymer material, which comprises a cationic polymer and a polyphosphate mixture comprising polyphosphates of varying chain lengths, wherein said active pharmaceutical ingredient has increased dissolution rate. In other embodiments, a microcapsule composition comprises microcapsules of an active pharmaceutical ingredient in a coacervated polymer material, which comprises a cationic polymer and a polyphosphate mixture comprising medium and long chain polyphosphates, wherein said active pharmaceutical ingredient has increased dissolution rate. In other embodiments, a microcapsule composition comprises microcapsules of an active pharmaceutical ingredient in a coacervated polymer material, which comprises a cationic polymer and a polyphosphate mixture comprising short and long chain polyphosphates, wherein said active pharmaceutical ingredient has increased dissolution rate. In other embodiments, a microcapsule composition comprises microcapsules of an active pharmaceutical ingredient in a coacervated polymer material, which comprises a cationic polymer and a polyphosphate mixture comprising short and medium chain polyphosphates, wherein said active pharmaceutical ingredient has increased dissolution rate. In some embodiments, a microcapsule composition comprises microcapsules of an active pharmaceutical ingredient in a coacervated polymer material, which comprises gelatin and an anionic polymer mixture comprising anionic polymers of varying lengths, wherein said active pharmaceutical ingredient has increased dissolution rate. In some embodiments, a microcapsule composition comprises microcapsules of an active pharmaceutical ingredient in a coacervated polymer material, which comprises gelatin and a polyphosphate mixture comprising polyphosphates of varying chain lengths, wherein said active pharmaceutical ingredient has increased dissolution rate. In some embodiments, a microcapsule composition comprises microcapsules of an active pharmaceutical ingredient in a coacervated polymer material, which comprises gelatin and a polyphosphate mixture comprising medium and long chain polyphosphates, wherein said active pharmaceutical ingredient has increased dissolution rate. In some embodiments, a microcapsule composition comprises microcapsules of an active pharmaceutical ingredient in a coacervated polymer material, which comprises gelatin and a polyphosphate mixture comprising short and medium chain polyphosphates, wherein said active pharmaceutical ingredient has increased dissolution rate. In some embodiments, a microcapsule composition comprises microcapsules of an active pharmaceutical ingredient in a coacervated polymer material, which comprises gelatin and a polyphosphate mixture comprising short and long chain polyphosphates, wherein said active pharmaceutical ingredient has increased dissolution rate. In each of the above embodiments, the increased dissolution rate is relative to a prior art microcapsule composition including prior art microcapsule compositions having cellulose based coatings.

In some embodiments of the present invention, a microcapsule composition comprises microcapsules of an active pharmaceutical ingredient in a coacervated polymer material comprising a cationic polymer and an anionic polymer mixture, wherein said anionic polymer mixture comprises anionic polymers of varying lengths and wherein said microcapsule composition has increased dissolution rate. In some embodiments, a microcapsule composition comprises microcapsules of an active pharmaceutical ingredient in a coacervated polymer material, which comprises a cationic polymer and a polyphosphate mixture comprising polyphosphates of varying chain lengths, wherein said microcapsule composition has increased dissolution rate. In other embodiments, a microcapsule composition comprises microcapsules of an active pharmaceutical ingredient in a coacervated polymer material, which comprises a cationic polymer and a polyphosphate mixture comprising medium and long chain polyphosphates, wherein said microcapsule composition has increased dissolution rate. In other embodiments, a microcapsule composition comprises microcapsules of an active pharmaceutical ingredient in a coacervated polymer material, which comprises a cationic polymer and a polyphosphate mixture comprising short and long chain polyphosphates, wherein said microcapsule composition has increased dissolution rate. In other embodiments, a microcapsule composition comprises microcapsules of an active pharmaceutical ingredient in a coacervated polymer material, which comprises a cationic polymer and a polyphosphate mixture comprising short and medium chain polyphosphates, wherein said microcapsule composition has increased dissolution rate. In some embodiments, a microcapsule composition comprises microcapsules of an active pharmaceutical ingredient in a coacervated polymer material, which comprises gelatin and an anionic polymer mixture comprising anionic polymers of varying lengths, wherein said microcapsule composition has increased dissolution rate. In some embodiments, a microcapsule composition comprises microcapsules of an active pharmaceutical ingredient in a coacervated polymer material, which comprises gelatin and a polyphosphate mixture comprising polyphosphates of varying chain lengths, wherein said microcapsule composition has increased dissolution rate. In some embodiments, a microcapsule composition comprises microcapsules of an active pharmaceutical ingredient in a coacervated polymer material, which comprises gelatin and a polyphosphate mixture comprising medium and long chain polyphosphates, wherein said microcapsule composition has increased dissolution rate. In some embodiments, a microcapsule composition comprises microcapsules of an active pharmaceutical ingredient in a coacervated polymer material, which comprises gelatin and a polyphosphate mixture comprising short and medium chain polyphosphates, wherein said microcapsule composition has increased dissolution rate. In some embodiments, a microcapsule composition comprises microcapsules of an active pharmaceutical ingredient in a coacervated polymer material, which comprises gelatin and a polyphosphate mixture comprising short and long chain polyphosphates, wherein said microcapsule composition has increased dissolution rate. In each of the above embodiments, the increased dissolution rate is relative to a prior art microcapsule composition including prior art microcapsule compositions having cellulose based coatings.

In some embodiments, the microcapsule coating thickness is about 5 µm to about 40 µm. In some preferred embodiments, the minimum microcapsule coating thickness is about 10 µm.

Applications

The microcapsules produced by the processes of the present invention may be used to prepare liquids, as free-flowing powders or compressed solids, to store a substance, to separate reactive substances, to reduce toxicity of a substance, to protect a substance against oxidation, to deliver a substance to a specific environment and/or control the rate of release of a substance. In preferred embodiments, the microcapsules of the present invention may be used to deliver a biologically active substance to an organism for medical or nutritional purposes. The organism is preferably a mammal, more preferably a human. The microcapsules may be used in any desired application without further processing. Microcapsules containing the biologically active substance may be included, for example, in foods or beverages or in drug delivery systems or pharmaceutical formulations.

The term "pharmaceutical formulation" as used herein refers to formulations containing the microcapsules of the invention in combination with carriers or excipients suited to a selected drug delivery platform, e.g., an orally dispersible formulation, an effervescent formulation, a chewable tablet, a lozenge, a hard or swallow tablet, or the like.

"Carriers" or "vehicles" as used herein refer to carrier materials suitable for oral drug administration, and include any such materials known in the art, e.g., diluents, binders, granulating agents, disintegrants, lubricating agents, colorants, flavoring agents, and the like.

Various types of pharmaceutical formulations may be prepared using the presently disclosed microcapsules, including powders, chewable tablets, orally dissolving tablets, effervescent formulations, and liquid dispersions. For solid formulations such as powders, chewable tablets, orally dissolving tablets and effervescent formulations, conventional carriers, excipients and additives can be employed, including diluents, binders, granulating agents, disintegrants, flavoring additives, and the like. Examples of the normally employed excipients include pharmaceutical grades of mannitol, lactose, starch, and the like. Liquid pharmaceutical compositions containing the present microcapsules will generally be prepared by dispersing or suspending the microcapsules in a non-aqueous carrier which does not cause release of the drug, or else by dispersing the microcapsules in an aqueous carrier immediately prior to administration to the patient. For example, the microcapsules may be provided as a free-flowing particulate material, as in a sachet or other suitable package, and such a particulate material may be dispersed in an aqueous carrier. These solid or liquid formulations may contain any amount of the microcapsules needed to provide the desired amount of the active ingredient contained in the microcapsules. For example, amounts of microcapsules on the order of about 10 wt. % to about 95 wt. % of the dosage form may be used. Actual methods of preparing such dosage forms are known, or will be apparent, to those skilled in this art.

This application incorporates by reference U.S. provisional application No. 61/384,351 in its entirety.

It will be apparent to one of skill in the art that various modifications and variations can be made in the methods and compositions of the present invention without departing from the spirit or scope of the invention. Thus, it is intended that the present invention cover the modifications and variations of the present invention provided they come within the scope of the appended claims and their equivalents.

The following examples are given to illustrate the present invention. It should be understood, however, that the invention is not to be limited to the specific conditions or details described in these examples. Throughout the specification, any and all referenced publicly available documents, including but not limited to a U.S. patent, are specifically incorporated by reference.

EXAMPLES

Example 1

| Ingredient | % | Grams |
|---|---|---|
| Gelatin, type A 225 bloom | 2.0% | 20 |
| Sodium Polyphosphate | 0.2% | 2.0 |
| Acetaminophen (Covidien, Special Granular) | 20% | 200.0 |
| Purified Water | Quantity sufficient to make 1000 ml | |
| Transglutaminase | | 4 |

In a 2000 ml Kimax beaker using a 3.5 inch diameter A310 Lightnin mixer blade, gelatin was mixed with 700 ml of water and heated to 40 C with stirring at ~300 RPM. When gelatin was dissolved, acetaminophen ("ApAp") was added and mixed until acetaminophen was fully wetted. The mixture was heated to 50° C. to 55° C. The sodium polyphosphate was dissolved in ~200 ml water while stirring. When dissolved, the polyphosphate solution was added to the gelatin acetaminophen solution and reheated to ~50° C. Sufficient volume of water was added to make a total of 1000 ml water ("ApAp/gelatin/polyphosphate mixture"). The pH of the mixture was adjusted to 4.8 using a dilute acid such as acetic acid while stirring at 400 RPM+/−25. The mixture was cooled to 10° C. at a cooling rate of 0.10 per minute. The transglutaminase was added to 20 ml of water and then added to the ApAp/gelatin/polyphosphate mixture at 10° C. and held at 10° C. for 4 hours. The slurry was heated to room temperature and held at room temperature for 8 hours. The slurry was transferred to a Buchner funnel and the supernatant removed under vacuum. The filtrate was washed twice with 200 mls of purified water. The washed filtrate was transferred to a Vector Fluid Bed Model MFL-0.1 and dried using an inlet temperature of 50° C. and an air flow of 200 to 400 Liters/minute to a moisture content of less than 2%.

Figure 5:
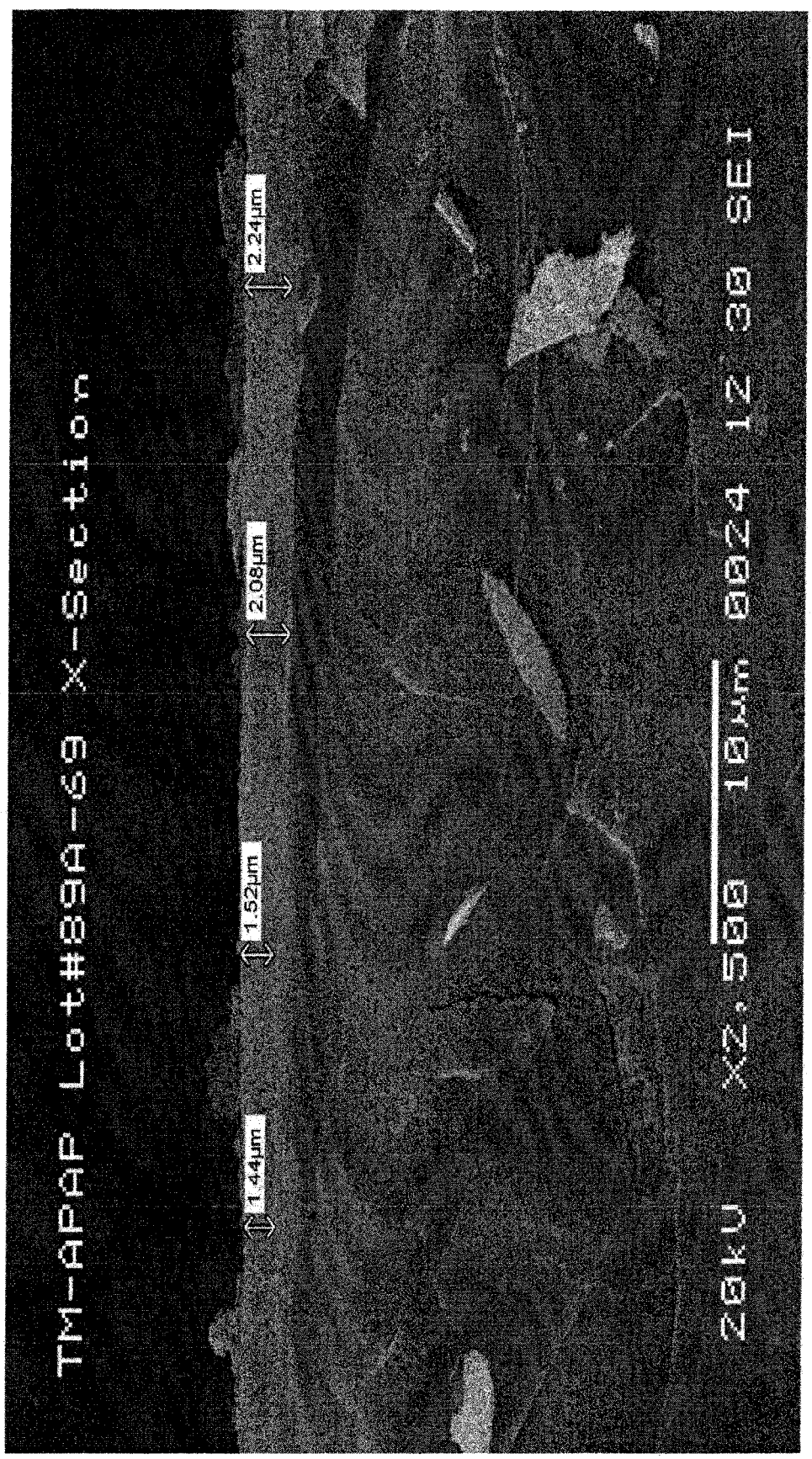
FIG. 5 illustrates an SEM of an exemplary microcapsule composition having taste mask properties and wherein the core material is acetaminophen and the polymeric coating includes gelatin, polyphosphate and transglutimase as described in Example 1.
Figure 6:
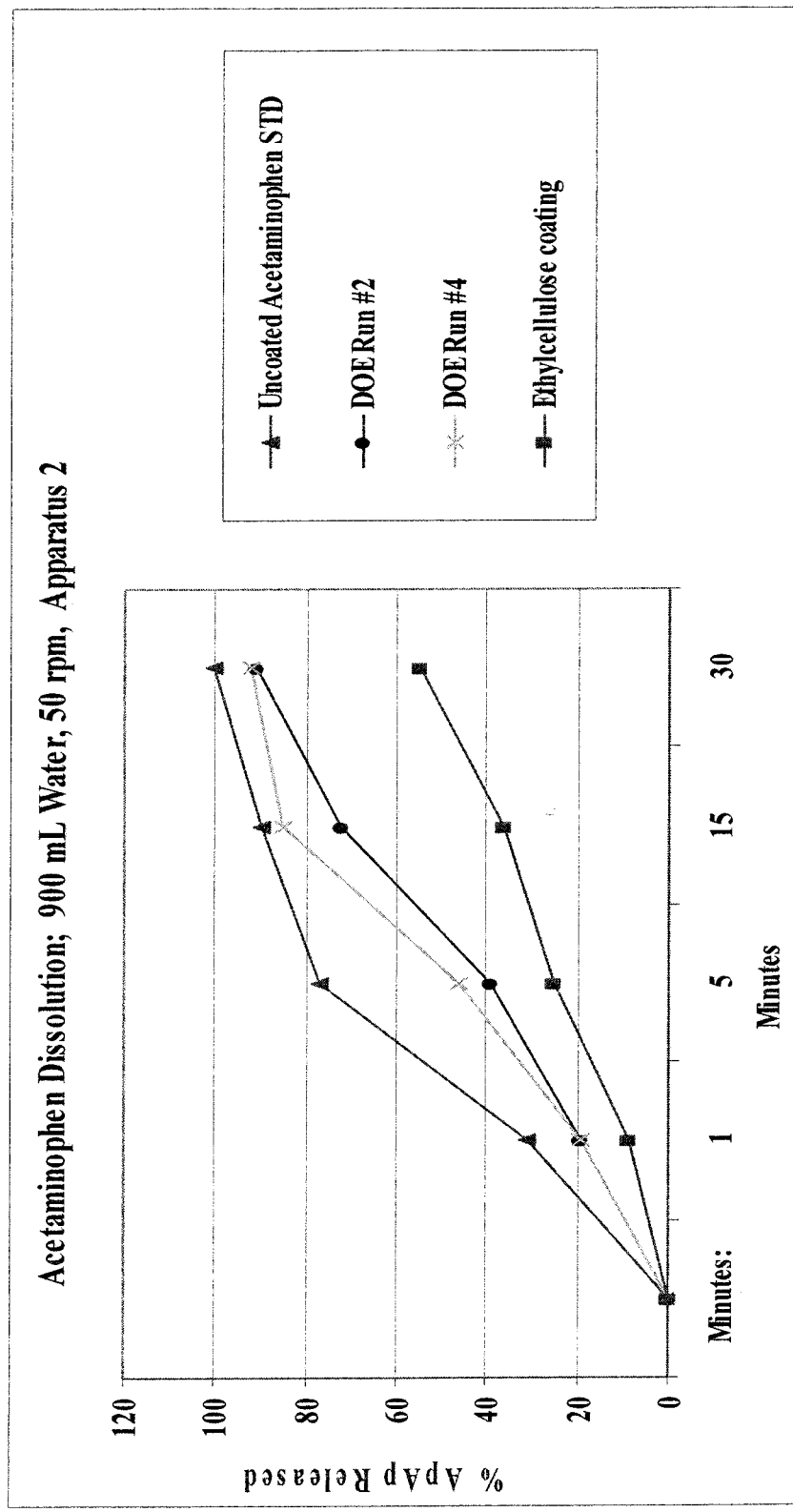
FIG. 6. illustrates the modified-release of acetaminophen from an embodiment of the present invention as described in Example 2 compared to prior art compositions.

An SEM of the product is illustrated in FIG. 5. The polymeric coating has a thickness ranging from 1.4 µm to 2.2 µm.

Example 2

| | |
|---|---|
| Gelatin A, 225 bloom, porcine | 0.90% (10 grams) |
| Acetaminophen (APAP) | 8.97% (100 grams) |
| Transglutaminase (Activa ® TI) | 0.36% (4 grams) |
| Polyphosphate mixture | 0.09% (1 gram) |
| Water | 89.69% (1000 grams) |
| Total | 100.00% |

Polyphosphate mixtures were prepared by adding Glass H and then Hexaphos (both from ICL Performance Products, St. Louis, Mo.) (at ratios of 40:60 or 55:45) to reverse osmosis (RO) water at room temperature, and mixed until dissolved. Gelatin (Great Lakes Gelatin Co., Graylakes, Ill.) was added to RO water at room temperature and mixed until dissolved. Gelatin solution was heated to either 50° C. or 60° C. Acetaminophen was added to gelatin solution, and then the polyphosphate mixture solution was added. The mixture was heated to 50° C. while mixing. When the temperature reached either 50° C. or 60° C., the pH was adjusted to either 4.5 or 4.8 using glacial acetic acid (at a 1:4 ratio with water). When the pH equaled either 4.5 or 4.8, the mixture was cooled to 10° C. at a rate of 1° C./10 min. Once the mixture reached 10° C., transglutaminase (Ajinomoto Food Ingredients LLC, Chicago, Ill.) was added, and mixed (at approximately 400 RPM with a Lightnin A310 turbine mixer) for 4 or 8 hours at 25° C. or 40° C., respectively. Each sample was decanted, washed twice with RO water, and then de-watered in Buchner funnel. The resultant samples were dried in Vector fluid bed dryer at 40° C. inlet temperature for 30 minutes and then screened through 20-mesh. Finished dry product was checked for particle size on a Malvern Mastersizer 2000 and compared to the characteristics of the core material. Losses on drying determinations were performed using an infrared LOD instrument at 120° C. for 10 minutes with a 2.0-3.0 gram sample.

| Run # | Polyphosphate Ratio | Temperature at pH adjust | pH | Cross-link conditions |
|---|---|---|---|---|
| 1 | 40:60 | 60° C. | 4.5 | 4 hrs., pH 4.5, 25° C. |
| 2 | 40:60 | 60° C. | 4.8 | 4 hrs., pH 4.5, 25° C. |
| 3 | 40:60 | 50° C. | 4.5 | 8 hrs., pH 5.0, 40° C. |
| 4 | 40:60 | 50° C. | 4.8 | 8 hrs., pH 5.0, 40° C. |
| 5 | 55:45 | 60° C. | 4.5 | 8 hrs., pH 5.0, 40° C. |
| 6 | 55:45 | 60° C. | 4.8 | 8 hrs., pH 5.0, 40° C. |
| 7 | 55:45 | 50° C. | 4.5 | 4 hrs., pH 4.5, 25° C. |
| 8 | 55:45 | 50° C. | 4.8 | 4 hrs., pH 4.5, 25° C. |

| Run # | Core d50 | d50 | Difference | Core SWM | SWM | Difference | Core VWM | VWM | Difference |
|---|---|---|---|---|---|---|---|---|---|
| 1 | 347 | 388 | 41 | 333 | 371 | 38 | 361 | 404 | 43 |
| 2 | 347 | 367 | 20 | 333 | 357 | 23 | 361 | 378 | 17 |
| 3 | 347 | 742 | 395 | 333 | 702 | 369 | 361 | 794 | 433 |
| 4 | 347 | 366 | 19 | 333 | 353 | 20 | 361 | 380 | 19 |
| 5 | 347 | 660 | 313 | 333 | 633 | 299 | 361 | 691 | 330 |
| 6 | 347 | 528 | 181 | 333 | 495 | 162 | 361 | 559 | 198 |
| 7 | 347 | 463 | 116 | 333 | 438 | 105 | 361 | 486 | 125 |
| 8 | 347 | 469 | 122 | 333 | 444 | 111 | 361 | 493 | 132 |

Results showed that the combination of factors used in Run #2 and Run #4 represent a coating thickness of approximately 10 µm, close to the theoretical coating thickness expected. A theoretical coating thickness of 10% of the core material (17 µm) was expected since each run contained 10% of solids. The runs with differences ranging from 116 to 395 indicate a significant amount of unwanted agglomeration. SWM refers to the surface weight mean particle size. VWM refers to the weight mean particle size.

| | | | Minutes: | | |
|---|---|---|---|---|---|
| Acetaminophen Dissolution 900 mL Water, 50 rpm, Apparatus 2 | 1 | 5 | 15 | 30 |
| | Percent (%) Drug Released | | | | |
| Uncoated Acetaminophen STD | 0 | 31 | 77 | 90 | 100 |
| DOE Run #2 | 0 | 19 | 39 | 72 | 91 |
| DOE Run #4 | 0 | 19 | 46 | 85 | 92 |
| Ethylcellulose coating | 0 | 9 | 25 | 36 | 55 |

Acetaminophen dissolution was compared between microcapsules prepared from Run #2 and Run #4, an uncoated acetaminophen standard and a commercial acetaminophen coated with ethylcellulose by USP dissolution method for Acetaminophen (900 mL water, 50 rpm, Apparatus 2). As illustrated in FIG. 5, samples, corresponding to DOE Run #2 and DOE Run #4, showed improved functionality of API (acetaminophen) as shown by faster dissolution of acetaminophen with the microencapsulation system described herein compared to prior art microcapsules having ethylcellulose coatings.

Example 3

| Gelatin, 225 bloom, porcine | 0.99% (11 grams) |
|---|---|
| Acetaminophen (APAP) | 8.96% (100 grams) |
| Transglutaminase (Activa ® TI) | 0.36% (4 grams) |
| Polyphosphate mixture | 0.09% (1 gram) |
| Water | 89.61% (1000 grams) |
| Total | 100.00% |

A polyphosphate mixture was prepared by adding Glass H and then Hexaphos (both from ICL Performance Products, St. Louis, Mo.) (at ratio of 75:25) to reverse osmosis (RO) water at room temperature, and mixed until dissolved. Gelatin (Great Lakes Gelatin Co., Graylakes, Ill.) was added to RO water at room temperature and mixed until dissolved. Gelatin solution was heated to 50° C. Acetaminophen was added to gelatin solution, and then the polyphosphate mixture solution was added. The mixture was heated to 60° C. while mixing. When the temperature reached 60° C., the pH was adjusted to 4.5 using glacial acetic acid (at a 1:4 ratio with water). When the pH equaled 4.5, the suspension was mixed (at approximately 301 RPM with a Lightnin A310 turbine mixer) while cooling at a rate of 1° C./10 min. Once the mixture reached 45° C., many agglomerates were observed. Once the mixture reached 22° C. the batch was discontinued due to excessive agglomeration.

Example 4

| Gelatin, 225 bloom, porcine | 0.99% (11 grams) |
|---|---|
| Acetaminophen (APAP) | 8.96% (100 grams) |
| Transglutaminase (Activa ® TI) | 0.36% (4 grams) |
| Polyphosphate mixture | 0.09% (1 gram) |
| Water | 89.61% (1000 grams) |
| Total | 100.00% |

A Polyphosphate mixture was prepared by adding Glass H and then Hexaphos (both from ICL Performance Products, St. Louis, Mo.) (at ratio of 25:75) to reverse osmosis (RO) water at room temperature, and mixed until dissolved. Gelatin (Great Lakes Gelatin Co., Graylakes, Ill.) was added to RO water at room temperature and mixed until dissolved. Gelatin solution was heated to 50° C. Acetaminophen was added to gelatin solution, and then the polyphosphate mixture solution was added. The mixture was heated to 50° C. while mixing. When the temperature reached 50° C., the pH was adjusted to 4.5 using glacial acetic acid (at a 1:4 ratio with water). When the pH equaled 4.5, the suspension was mixed (at approximately 306 RPM with a Lightnin A310 turbine mixer) while cooling at a rate of 1° C./10 min. Once the mixture reached 10° C., transglutaminase (Ajinomoto Food Ingredients LLC, Chicago, Ill.) was added, and mixed (at approximately 306-316 RPM with a Lightnin A310 turbine mixer) for 4 hours at 10° C.

After 4 hours of mixing at 10° C., the pH was adjusted to 5.0 using sodium hydroxide N/5. When the pH equaled 5.0, the suspension was heated to 40° C. Once the mixture reached 40° C., it was cooled to room temperature, and mixed (at approximately 306-316 RPM with a Lightnin A310 turbine mixer) for approximately 10-12 hours.

The batch was decanted, washed twice with RO water, and then de-watered in Buchner funnel. The batch was split into four samples and either 1) blended with fumed silica in a bag before being added to a Vector fluid bed or 2) added directly to a Vector fluid bed with the fumed silica added to the top of the product in the fluid bed or 3) blended with talc in a bag before being added to a tray drier or 4) blended with fumed silica in a bag before being added to a Vector fluid bed. Resultant samples were dried in Vector fluid bed dryer at 40° C. inlet temperature for 30 minutes or in a tray dryer at 40° C. overnight and then screened through 20-mesh.

Finished dry product was checked for yield by sieving through a 20-mesh and a 30-mesh ASTM screen.

Finished dry product was checked for particle size on a Malvern Mastersizer 2000 and compared to the characteristics of the core material.

| Drying Run # | Core d50 | d50 | Difference | Core SWM | SWM | Difference | Core VWM | VWM | Difference |
|---|---|---|---|---|---|---|---|---|---|
| 1 | 347 | 481 | 134 | 333 | 450 | 117 | 361 | 507 | 146 |
| 2 | 347 | 466 | 119 | 333 | 440 | 107 | 361 | 490 | 129 |
| 3 | 347 | 445 | 98 | 333 | 420 | 87 | 361 | 468 | 107 |
| 4 | 347 | 438 | 91 | 333 | 416 | 83 | 361 | 459 | 98 |

Results showed that the combination of factors used represent a particle size increase of approximately 91 μm to 134 μm indicate a significant amount of unwanted agglomeration. A theoretical coating thickness of 10% of the core material (14 μm) was expected since each run contained 10% of solids.

Example 5

| | | |
|---|---|---|
| Gelatin, 225 bloom, porcine | 0.99% | (11 grams) |
| Acetaminophen (APAP) | 8.96% | (100 grams) |
| Transglutaminase (Activa ® TI) | 0.36% | (4 grams) |
| Polyphosphate mixture | 0.09% | (1 gram) |
| Water | 89.61% | (1000 grams) |
| Total | 100.00% | |

A Polyphosphate mixture was prepared by adding Glass H and then Hexaphos (both from ICL Performance Products, St. Louis, Mo.) (at ratio of 50:50) to reverse osmosis (RO) water at room temperature, and mixed until dissolved. Gelatin (Great Lakes Gelatin Co., Graylakes, Ill.) was added to RO water at room temperature and mixed until dissolved. Gelatin solution was heated to 50° C. Acetaminophen was added to gelatin solution, and then the polyphosphate mixture solution was added. The mixture was heated to 50° C. while mixing. When the temperature reached 50° C., the pH was adjusted to 4.5 using glacial acetic acid (at a 1:4 ratio with water). When the pH equaled 4.5, the suspension was mixed (at approximately 301 RPM with a Lightnin A310 turbine mixer) while cooling at a rate of 1° C./10 min. Once the mixture reached 44° C., excessive agglomeration was observed and the batch was discontinued due to agglomeration.

Example 6

| | |
|---|---|
| Gelatin, type A | 2.6 grams |
| Ibuprofen | 60 grams |
| Transglutaminase | 2.9 grams |
| gum Arabic | 3.6 grams |
| Water | 700 grams |
| Total | 100.00% |

Using a two inch diameter radial impeller in a four inch diameter one liter tall form glass beaker (Fisher FB-102-1000), water was added and heated to 50° C. Gelatin and gum Arabic were then added and dissolved. Ibuprofen was added and stirred at 600 RPM to fully wet powder. The pH was then adjusted to 4.5 using dilute acetic acid. Stirring was continued and the suspension was cooled at approximately 1° C. every 10 minutes until reaching 10° C. The transglutaminase was then added and the mixture allowed to stir as it warmed to room temperature with stirring continued overnight. The suspension was poured onto a Whatman #1 filter paper in a Buchner funnel and vacuum was drawn to remove supernatant. The filtrate was washed and then dried in tray drier at 50° C. to a moisture content of <2%.

Example 7

| | | |
|---|---|---|
| Gelatin A, 225 bloom, porcine | 0.90% | (10 grams) |
| Acetaminophen (APAP) | 8.97% | (100 grams) |
| Transglutaminase (Activa ® TI) | 0.36% | (4 grams) |
| Polyphosphate mixture | 0.09% | (1 gram) |
| Water | 89.69% | (1000 grams) |
| Total | 100.00% | |

Gelatin was mixed in 1000 ml of water at room temperature in a 2000 ml (5 inch diameter) beaker (Kimax #14005) using an overhead stirrer with a 3.25 inch diameter A310 Lightnin mixer blade at 400 RPM (+/−25). Acetaminophen was added and stirred to fully wet the powder. A polyphosphate mixture was added and allowed to dissolve. The pH was then adjusted to 4.8 using dilute acetic acid. Stirring was continued and the suspension was cooled at approximately 1° C. for 10 minutes until the temperature is 10° C. The transglutaminase was then added and the mixture allowed to stir as it warms to room temperature and stirring continued overnight. The suspension was poured onto a Whatman #1 filter paper in a filtering funnel and vacuum is drawn to remove supernatant. Filtrate was then washed with two portions of 200 ml of deionized water and sucked dry. The was filtrate was dried at an inlet temperature of 50° C. and an air flow of 380 Liters/min in a Vector MFL-0.01 Model (Vector Corp, Marion, Iowa) fluid bed dryer to a moisture of <1%.

Example 8

| Ingredient | % | Kilograms |
|---|---|---|
| Gelatin, type A 225 bloom | 2.23 | 10.2 |
| Sodium Polyphosphate | 0.27 | 1.226 |
| Acetaminophen (Covidien, Special Granular) | 26.7 | 121.5 |
| Purified Water | ~70.5 | 323 |
| Transglutaminase | N/A | 2-3 |

In a 200 gallon stainless steel reaction vessel water was added and heated to 42° C. while stirring at 120 RPM using a A310 agitator. Upon the water reaching 35° C., gelatin was added followed by the polyphosphate mixture. Once the temperature reaches above 40° C., the acetaminophen was added. The pH of the system was adjusted to 4.8 using glacial acetic acid. The temperature of the system was cooled at 10° C. at a rate of 0.1 to 0.3° C./min. Once at the 10° C. the crosslinker transglutaminase was added and the system was held for 0.5 to 1 hours. Upon completion of the hold at 10° C., the system was warmed to 25° C. for 3 hours. After 3 hours the system was dried via centrifugation and fluid bed drying to a LOD of not more than 1.5%. SEM images of the product were obtained and are illustrated in FIGS. 2-5.

Example 9

Dissolution Testing of Orally Dispersible Ibuprofen Powder Stick Pak

A USP apparatus IV flow through cell was used to measure the dissolution of three orally dispersible powder blends of Ibuprofen. Powder blends were made up of: Example 6 (SPI Pharma); uncoated Ibuprofen 50 (BASF, Florham Park, N.J.); and Dasan Medichem (Soul, Korea) taste-masked Ibuprofen. Each sample was weighed and mixed by the process of spatulation until mixed. This mixture was passed through #30 mesh ASTM and packed in stick packs.

| Batch no | ODP based on Example 6 | Uncoated Ibuprofen 50 | Dasan Coated Ibuprofen |
| --- | --- | --- | --- |
| Quantity of Ibuprofen taken (in mg) | 218.22 | 200.20 | 242.30 |
| Quantity of sample taken (in mg) | 531.78 | 549.80 | 507.70 |
| TOTAL | 750.00 | 750.00 | 750.00 |

An amount of sample equivalent to contain 200 mg of Ibuprofen was weighed out and placed in the bead mixture of the flow through cell. At a rate of 16 ml/min, a 37° C. pH 7.2 phosphate buffer was pumped through cell and the effluent from the cell was collected in a reservoir vessel and samples removed for subsequent analysis in HPLC for Ibuprofen content at the time point specified. The data is an average of two determinations.

| Product | Ibuprofen ODP 200 mg |
| --- | --- |
| API | Ibuprofen |
| Apparatus | USP IV |
| Media | Phosphate buffer pH 7.2 |
| Volume | 900 mL |
| Flowrate | 16 mL/min |

Figure 7:
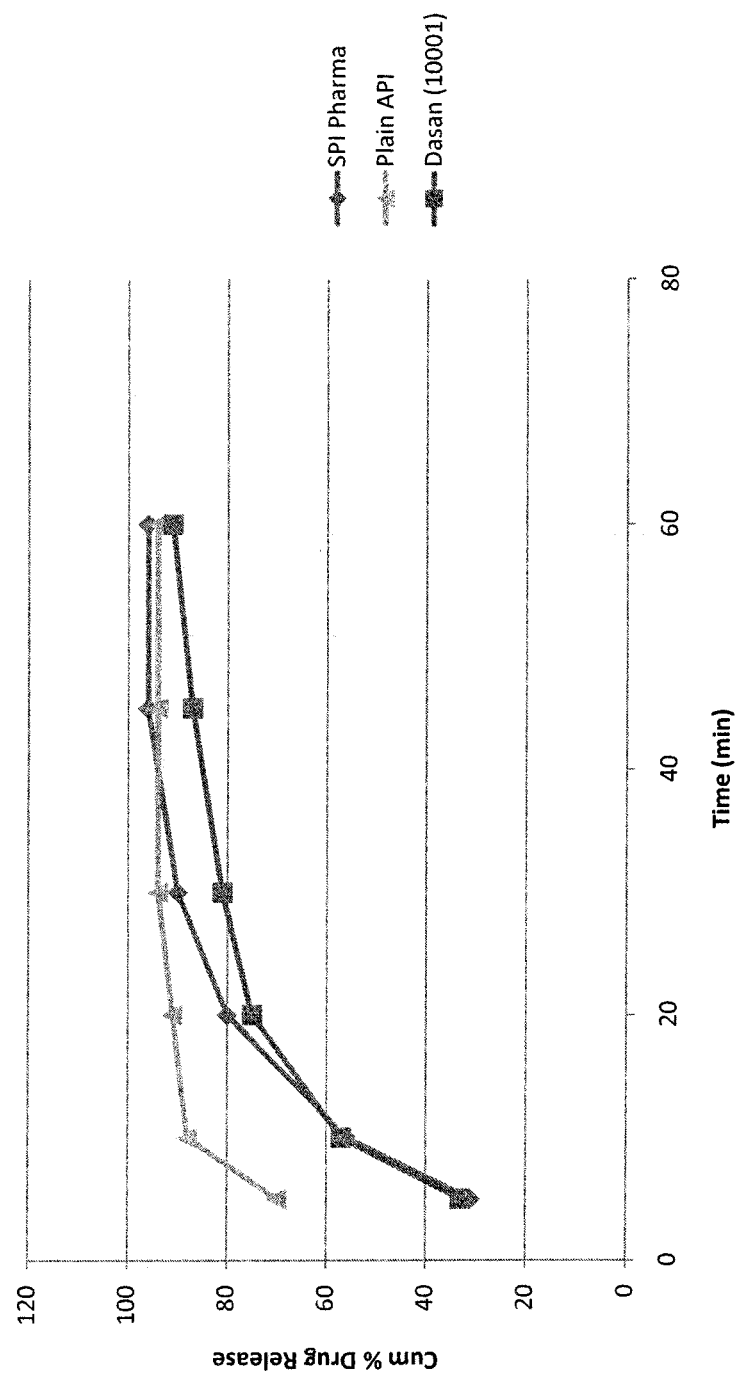
FIG. 7. illustrates the modified-release of ibuprofen from an embodiment of the present invention, as described in Example 8, compared to uncoated ibuprofen.

The dissolution of Ibuprofen over time for each sample is shown in the below table and graphically in FIG. 7.

| Product | Ibuprofen ODP 200 mg | | Ibuprofen ODP 200 mg | | Ibuprofen ODP 200 mg | |
| --- | --- | --- | --- | --- | --- | --- |
| API | SPI Pharma | | Plain API | | Dasan (10001) | |
| Apparatus | USP IV | | USP IV | | USP IV | |
| Media | Phosphate buffer pH 7.2 | | Phosphate buffer pH 7.2 | | Phosphate buffer pH 7.2 | |
| Volume | 900 mL | | 900 mL | | 900 mL | |
| Flowrate | 16 mL/min | | 16 mL/min | | 16 mL/min | |
| Time (min) | % | Time (min) | % | Time (min) | % | |
| 5 | 31 | 5 | 70 | 5 | 33 | |
| 10 | 56 | 10 | 88 | 10 | 57 | |
| 20 | 80 | 20 | 91 | 20 | 75 | |
| 30 | 90 | 30 | 94 | 30 | 81 | |
| 45 | 96 | 45 | 94 | 45 | 87 | |
| 60 | 96 | 60 | 94 | 60 | 91 | |

Example 10

Dissolution Testing of Orally Dispersible Powder Stick Pak

A USP apparatus IV flow through cell was used to measure the dissolution of three orally dispersible powder blends of acetaminophen. Powder blends were made up of: Example 7 (SPI Pharma); uncoated Acetaminophen (Covidien, St. Louis, Mo.)) special granular; and Eurand (Dayton, Ohio) taste-masked Acetaminophen. Each sample was weighed and mixed by the process of spatulation until mixed. This mixture was passed through #30 mesh ASTM and packed in stick packs.

| Batch no | Example 7 | uncoated Acetaminophen | Eurand Coated Acetaminophen |
| --- | --- | --- | --- |
| Quantity of Sample (in mg) | 173.81 | 160.00 | 173.40 |
| Quantity of sample taken (in mg) | 636.19 | 650.00 | 636.60 |
| TOTAL | 810.00 | 810.00 | 810.00 |

An amount of sample equivalent to contain 160 mg of Acetaminophen was weighed out and placed in the bead mixture of the flow through cell. At a rate of 16 ml/min, a 37° C. pH 5.8 phosphate buffer was pumped through cell and the effluent from the cell was collected in a reservoir vessel and samples removed for subsequent analysis in HPLC for Acetaminophen content at the time point specified. The data is an average of two determinations.

| Product | APAP ODP 160 mg |
| --- | --- |
| API | Acetaminophen |
| Apparatus | USP IV |
| Media | Phosphate buffer pH 5.8 |
| Volume | 900 mL |
| Flowrate | 16 mL/min |

Figure 8:
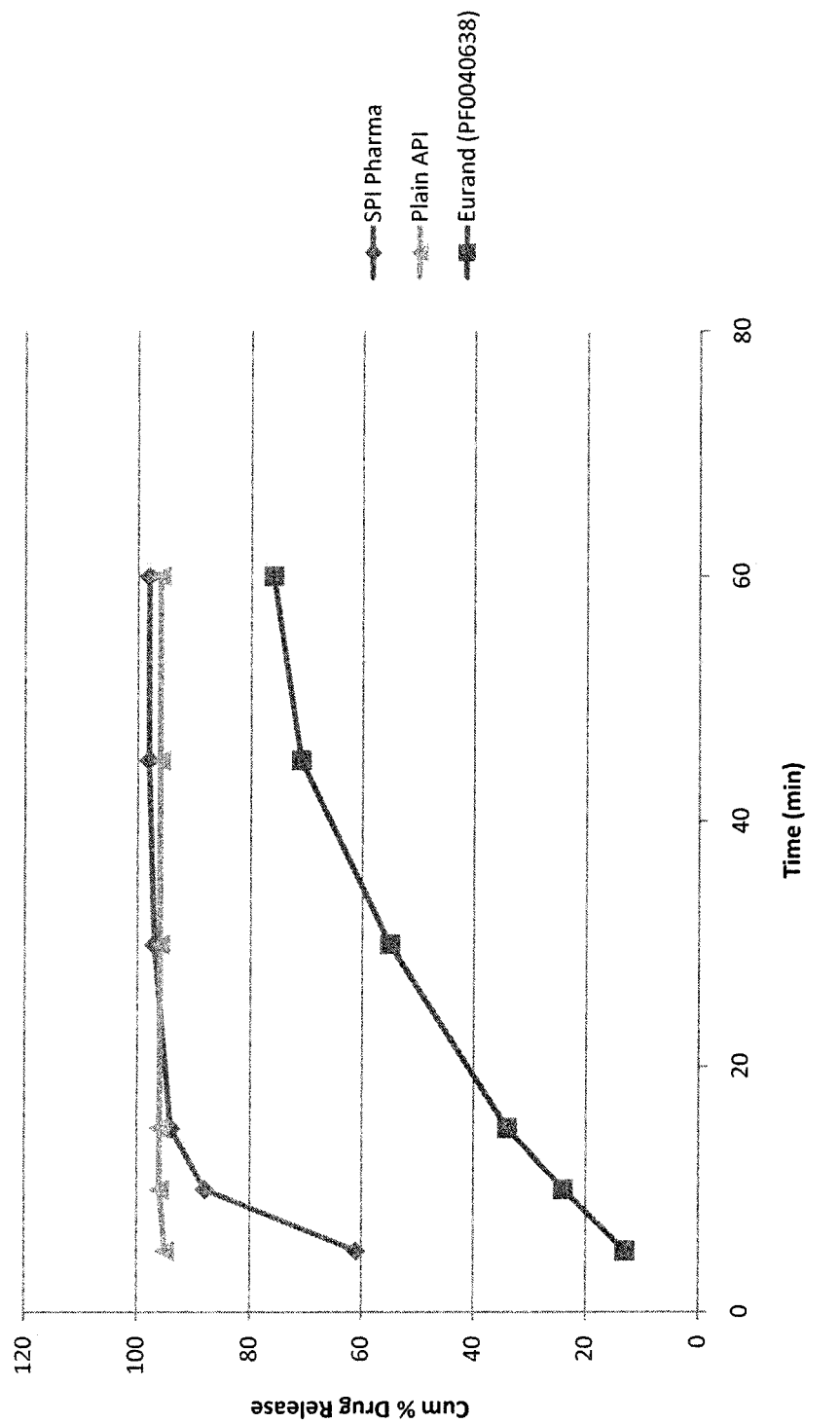
FIG. 8. illustrates the modified-release of acetaminophen from an embodiment of the present invention, as described in Example 9, compared to uncoated acetaminophen.

The dissolution of Acetaminophen over time for each sample is shown in the below table and graphically in FIG. 8.

| Product | APAP ODP 160 mg | | APAP ODP 160 mg | | APAP ODP 160 mg | |
| --- | --- | --- | --- | --- | --- | --- |
| API | Example 7 | | Uncoated Acetaminophen | | Eurand Coated Acetaminophen | |
| Apparatus | USP IV | | USP IV | | USP IV | |
| Media | Phosphate buffer pH 5.8 | | Phosphate buffer pH 5.8 | | Phosphate buffer pH 5.8 | |
| Volume | 900 mL | | 900 mL | | 900 mL | |
| Flowrate | 16 mL/min | | 16 mL/min | | 16 mL/min | |
| Time (min) | % | Time (min) | % | Time (min) | % | |
| 5 | 61 | 5 | 95 | 5 | 13 | |
| 10 | 88 | 10 | 96 | 10 | 24 | |
| 15 | 94 | 15 | 96 | 15 | 34 | |
| 30 | 97 | 30 | 96 | 30 | 55 | |

-continued

| | | | | | |
|---|---|---|---|---|---|
| 45 | 98 | 45 | 96 | 45 | 71 |
| 60 | 98 | 60 | 96 | 60 | 76 |

Example 11

An Orally Disintegrating Tablet ("ODT"), based on the microcapsule composition of Example 7, was prepared at four different compression pressures, 65, 97, 120 and 162 MPa, using a Globe Minipress at 26 RPM. Tablet weight was 800 mg and the tooling used was 0.5512 inch diameter flat faced beveled edged tooling.
21.978% Acetaminophen microcapsule according to Example 7

| | | |
|---|---|---|
| 72.772% | Pharmaburst 500 112-1253 | SPI Pharma |
| 2.5% | Sodium Stearyl Fumerate 550-1100 | SPI Pharma |
| 0.75 | Sucralose | Tate & Lyle |
| 2.0% | Bubblegum Flavor | Givauden |

Each ODT exhibited taste masking properties.

Example 12

Wurster Coating
Coating solution (1); 4.5% gelatin solution
Solution (2); 5.0% glutaraldehyde solution
Coated Core: Ibuprofen (Shandong Xinhau) 150 um (Vwm)

| Material | % | Gm |
|---|---|---|
| Gelatin Type A 225 bloom strength | 4.5% | 45 |
| Sodium Polyphosphate | 0.5% | 5 |
| Talc | 1.0% | 10 |
| Purified water qs | 100% | 1000 |

Gelatin is added to water at 40° C. to 50° C. and stirred until dissolved. Sodium polyphosphate is added and mixed to dissolve. Temperature is maintained at 50° C. and pH adjusted to 4.8 with hydrochloric acid.

Equipment Setup

| | |
|---|---|
| Nozzle bore | 1.2 mm |
| Distance Wurster/bottom | 15 mm |
| Atomizing Air | 2 bar |
| Filter cleaning time | 5 sec |
| Filter cleaning interval | 45 sec |
| Drying Air Volume | >45-90 M3/h |
| Inlet temperature | 30-50 C. |
| Exhaust temperature | 20-27 C. |
| Product Temperature | 20-27 C. |
| Spray rate | 4 to 10 g/min/kg |

Gelatin solution is sprayed onto Ibuprofen cores at a spray rate and inlet temperature that keeps the particles fluidized and the product temperature between 25° C. to 38° C. A 20% to 30% hydration level (ramp) is maintained in polymer to keep polymer moistened. Up to 1% talc is added, if needed, to maintain fluidization. The solution is sprayed until solution is gone.

Using an inlet temperature of 30° C. to 35° C., 80 mls of a 5.0% glutaraldhyde solution is sprayed onto coated cores at 4 to 8 ml/min/kilo. Bed dried to a moisture content of 3% to 4% and parked for 2 hours (mix using air flow every 15 minutes). pH of particles is checked. Sufficient dilute solution of HCL is sprayed onto particles to adjust pH to 4.5 pH using the same parameters as for the glutaraldehyde solution spraying, and dried at 45° C. until product moisture content reaches less than 2%. Material is discharged and screened through US mesh 20 screen.

We claim:

1. A composition comprising:
   a core material having a taste value;
   a polymeric coating substantially surrounding the core material, the polymeric coating comprising a coacervated polymer material comprising a cationic polymer, the cationic polymer comprising gelatin, and an anionic polymer mixture, the anionic polymer mixture comprising a long chain polyphosphate in combination with a medium chain polyphosphate, wherein the ratio of the cationic polymer to the anionic polymer mixture ranges from 8:1 to 11:1 and the polymeric coating has a thickness selected from between 1 μm to 20 μm, wherein the thickness of the polymeric coating is uniform and varies over a range from 0.2 μm to 2.0 μm;
   wherein the composition provides a controlled release of a portion of the core material which is taste masked over a time period ranging from 0.5 minute to 2 minutes in the oral cavity and provides release of the remaining core material in a gastrointestinal tract.

2. The composition of claim 1, wherein the composition has a microcapsule form.

3. The composition of claim 1, wherein the polymeric coating is hydrophilic.

4. The composition of claim 1, wherein said polymer further comprises a crosslinking agent.

5. The composition of claim 1, wherein the core material comprises an active pharmaceutical ingredient.

6. The composition of claim 5, wherein said active pharmaceutical ingredient is selected from the group consisting of acetaminophen, ibuprofen, dexibuprofen lysinate, naproxen, loperamide, dimenhydrinate, doxylamine, dextromethorphan and chlorpheniramine.

7. The composition of claim 1, wherein the gelatin is selected from the group consisting of: gelatin type A, gelatin type B, gelatin hydrolysates, gelatin succinylates and mixtures thereof.

8. The composition of claim 1, wherein the core material has a water solubility taste threshold and an associated pH of less than or equal to 6; and wherein the polymeric coating has a pH value less than or equal to the associated pH of the water solubility taste threshold.

9. The composition of claim 8, wherein the water solubility taste threshold ranges from $1 \times 10^{-4}$ mol/L to $1 \times 10^{-1}$ mol/L.

10. The composition of claim 1, wherein the core material has a water solubility taste threshold and an associated pH of greater than or equal to 6; and wherein the polymeric coating has a pH value less than or equal to the associated pH of the water solubility taste threshold.

11. The composition of claim 10, wherein the water solubility taste threshold ranges from $1 \times 10^{-4}$ mol/L to $1 \times 10^{-1}$ mol/L.

12. A pharmaceutical formulation comprising the composition according to claim 1 and further comprising one or more pharmaceutically acceptable ingredients independently selected from the group consisting of: excipients, binders, lubricants, disintegrating agents, sugar alcohols, colors, flavors and combinations thereof.

13. The pharmaceutical formulation of claim 12, wherein the formulation is compressed into a tablet at a compression pressure of up to 160 MPa.

\* \* \* \* \*